(12) United States Patent
Abrams et al.

(10) Patent No.: US 6,492,118 B1
(45) Date of Patent: Dec. 10, 2002

(54) METHODS OF IMMOBILIZING LIGANDS ON SOLID SUPPORTS

(75) Inventors: Ezra S. Abrams, W. Newton; Tianhong Zhang, Framingham; Slawomir Mielewczyk, Newton; Brian C. Patterson, Waltham, all of MA (US)

(73) Assignee: Matrix Technologies Corporation, Hudson, NH (US)

( * ) Notice: Subject to any disclaimer, the term of this patent is extended or adjusted under 35 U.S.C. 154(b) by 0 days.

(21) Appl. No.: 09/649,637

(22) Filed: Aug. 28, 2000

Related U.S. Application Data

(60) Provisional application No. 60/151,267, filed on Aug. 27, 1999, and provisional application No. 60/177,844, filed on Jan. 25, 2000.

(51) Int. Cl.[7] ............................. C12Q 1/68; C12M 1/36; C12N 11/16; C07H 21/04; C07K 5/00

(52) U.S. Cl. .................... 435/6; 435/174; 435/283.1; 435/287.2; 435/287.9; 536/22.1; 536/23.1; 536/24.3; 536/25.3; 422/50; 422/60; 422/68.1; 530/300

(58) Field of Search .................. 435/6, 174, 287.2, 435/283.1, 287.9; 536/25.3, 22.1, 23.1, 24.3; 422/50, 61, 68.1

(56) References Cited

U.S. PATENT DOCUMENTS

| | | | |
|---|---|---|---|
| 4,667,025 A | 5/1987 | Miyoshi et al. ............... 536/27 |
| 4,683,202 A | 7/1987 | Mullis ......................... 435/91 |
| 4,789,737 A | 12/1988 | Miyoshi et al. ............... 536/27 |
| 4,820,812 A | 4/1989 | Miyoshi et al. ............... 536/27 |
| 4,898,824 A | 2/1990 | Yip ............................. 435/180 |
| 5,034,428 A | 7/1991 | Hoffman et al. ............... 522/5 |
| 5,176,966 A | 1/1993 | Epp et al. ..................... 429/26 |
| 5,324,650 A * | 6/1994 | Obzansky et al. ........... 435/188 |
| 5,478,893 A | 12/1995 | Ghosh et al. ................ 525/329 |
| 5,482,836 A | 1/1996 | Cantor et al. .................. 435/6 |
| 5,599,695 A | 2/1997 | Pease et al. ................ 435/91.1 |
| 5,728,296 A * | 3/1998 | Hjerten et al. ........... 210/198.2 |
| 5,807,522 A | 9/1998 | Brown et al. ................. 422/50 |
| 5,837,860 A * | 11/1998 | Anderson et al. .......... 536/25.3 |
| 5,858,653 A | 1/1999 | Duran et al. ................... 435/6 |
| 5,932,711 A | 8/1999 | Boles et al. ............... 536/22.1 |
| 6,013,440 A | 1/2000 | Lipshutz et al. ............... 435/6 |
| 6,030,782 A | 2/2000 | Anderson et al. ............. 435/6 |
| 6,040,138 A | 3/2000 | Lockhart et al. ............... 435/6 |
| 6,083,763 A | 7/2000 | Balch ......................... 436/518 |
| 6,093,370 A | 7/2000 | Yasuda et al. ............. 422/68.1 |
| 6,268,131 B1 * | 7/2001 | Kang et al. .................... 435/6 |

OTHER PUBLICATIONS

Salo et al. "Disulfide–tethered solid supports for synthesis of photoluminescent oligonucleotide conjugates: hydrolytic stability and labeling on the support" Bioconjugate Chemistry, 1998, 9: 365–371.*

Rehman et al. "Immobilization of acrylamide–modified oligonucleotides by co–polymerization", Nucleic Acid Research, vol. 27, No. 2, 1999.*

(List continued on next page.)

*Primary Examiner*—W. Gary Jones
*Assistant Examiner*—B J Forman
(74) *Attorney, Agent, or Firm*—Wood, Herron & Evans, LLP

(57) ABSTRACT

A method is provided for immobilizing a ligand, e.g., a nucleic acid, on a solid support. The method includes providing a solid support containing an immobilized latent thiol group, activating the thiol group, contacting the activated thiol group with a nucleic acid comprising an acrylamide functional group, and forming a covalent bond between the two groups, thereby immobilizing the nucleic acid to the solid support. Kits containing the solid supports and method of utilizing the solid supports are also provided.

9 Claims, 9 Drawing Sheets

OTHER PUBLICATIONS

Egholm, M., et al., "Peptide Nucleic Acids (PNA). Oligonucleotide Analogues with an Achiral Peptide Backbone," *J. Am. Chem. Soc.*, 114: 1895–1897 (1992).

Greene, T.W., and Wuts, P.G.M., "Protective Groups in Organic Systhesis," (John Wiley & Sons), pp. 279–308 (1991).

Horejsi, V., and Kocourek, J., "Studies on Phytohemagglutinins XVIII. Affinity Electrophoresis of Phytohemagglutinins," *Biochimica et Biophysica Acta*, 336: 338–343 (1974).

Joyce, G.F., "Amplification, mutation and selectionof catalytic RNA," *Gene*, 82: 83–87(1898).

Klug, S.J., and Famulok, M., "All you wanted to know about SELEX," *Molecular Biology Reports* 20: 97(1994).

Perbal, B., "SDS Gel Electrophoresis" in A Practical Guide to Molecular Cloning, $2^{nd}$ Edition, (John Wiley & Sons), pp. 15–17 (1988).

Quartin, R.S., and Wetmur, J.G., "Effect of Ionic Strength on the Hybridization of Oligodeoxynucleotides with Reduced Charge Due to Methylphosphonate Linkages to Unmodified Oligodeoxynucleotides Containing the Complementary Sequence," *Biochemistry* 28: 1040–1047 (1989).

Rose, S., "Applications of a Novel Microarraying System in Genomics Research and Drug Discovery," *Journal of Association for Laboratory Automation* 3(3): (1998).

Schnaar, R.L., et al., "Reversible Covalent Immobilization of Ligands and Proteins on Polyacrylamide Gels," *Analytical Biochem.* 151: 268–281 (1985).

Segel, I.H., "Enzymes" in Biochemical Calculations, $2^{nd}$ Edition, (John Wiley & Sons) pp. 241–244 (1976).

Summerton, J. and Weller, D., "Morpholino Antisense Oligomers: Design, Preparation, and Properties," *Antisense & Nucleic Acid Drug Development*, 7(3): 187–195 (1997).

Wetmur, J.G., "DNA Probes: Applications of the Principles of Nucleic Acid Hybridization," *Critical Rev. in Biochem & Mol. Bio.*, 26(3/4): 227–259 (1991).

Rehman, F.N., et al., "Immobilization of acrylamide–modified oligonucleotides by co–polymerization", *Nucleic Acids Research*, 27(2):649–355 (1999).

* cited by examiner

METHODS OF IMMOBILIZING LIGANDS ON SOLID SUPPORTS

RELATED APPLICATION(S)

This application claims the benefit of the Provisional Application with Serial No. 60/151,267 filed Aug. 27, 1999 and the Provisional Application with Serial No. 60/177,844 filed Jan. 25, 2000. The teachings of both cited applications are incorporated herein by reference in their entireties.

BACKGROUND OF THE INVENTION

A variety of assay systems utilize ligands, e.g., nucleic acids, immobilized on the surface of a solid support. Effective immobilization of the nucleic acids is difficult, both because a range of materials are used to form the solid supports utilized in these assays, and because individual assays have special requirements. Therefore, although a number of attachment mechanisms have been developed, none are universally acceptable and most exhibit notable deficiencies. Among other drawbacks, present methods tend to require large amounts of nucleic acids, have high background noise levels or lack versatility (Duran et al. U.S. Pat. No. 5,858,653 issued Jan. 12, 1999).

The reproducible production of solid supports containing immobilized nucleic acids can also be problematic. For example, a convenient method of attachment utilizes nucleic acids with acrylamide functional groups which can be copolymerized to polyacrylamide gel matrices by free radical polymerization. However, oxidation can affect the copolymerization process resulting in variability in the results achieved using different supports, even when prepared using the same materials. Moreover, long-term stability of supports containing immobilized ligands has been difficult to achieve, often limiting the period of use to shortly after preparation.

SUMMARY OF THE INVENTION

The present invention is based, at least in part, on the discovery of a novel and convenient method of immobilizing a ligand, e.g., a nucleic acid, on a solid support. The method utilizes a covalent bond formed between a thiol group immobilized on the solid support and an acrylamide functional group contained on the nucleic acid to immobilize the nucleic acid to the support. In a particular embodiment, the covalent bond formed is a sulfide, a thioether, bond. The solid support can contain a polymer layer.

The method and the supports it produces are advantageous in several respects. The method utilizes reagents which are both readily available and compatible with the types of analysis conducted with solid supports. Because the materials can be used in aqueous solutions, the need for special skills and sophisticated chemical apparatus are minimized. In addition, because the materials and the supports they form are quite stable, the reproducibility from support to support which has previously proved so difficult to achieve can be realized. This stability also permits the components forming the bond to be combined at different times. For example, because solid supports containing the latent thiol groups of the invention are extremely stable, they can be produced under consistent conditions for use at a later time. Prior to analysis, the latent thiol groups can be activated and contacted with the acrylamide modified nucleic acids to form a support containing immobilized nucleic acids. In a particular embodiment, the thiol groups are activated by contact with a reducing agent.

In one embodiment, the invention is directed to a method of immobilizing an affinity ligand on a solid support comprising providing a solid support comprising an immobilized thiol group, contacting the thiol group with a nucleic acid comprising an acrylamide functional group, and forming a covalent bond between the two groups, thereby immobilizing the ligand on the solid support.

In a particular embodiment, the ligand is a nucleic acid, a modified nucleic acid or a nucleic acid analog. The solid support can comprise a plurality of thiol groups. A plurality of ligands can be immobilized on the solid support. In alternate embodiments, the solid support is formed from glass, silica, ceramic, plastic or metal compounds. The solid support can comprises two or more spatially distinct regions, each region comprising a plurality of immobilized nucleic acids. The solid support can further comprise a polymer layer. In a particular embodiment, the solid support can comprise a microarray. The thiol groups can comprise disulfide groups.

In another embodiment, the invention is directed to a method of immobilizing an affinity ligand on a solid support comprising the steps of providing a solid support comprising immobilized latent thiol groups, activating the latent thiol groups, and reacting the activated thiol groups with an affinity ligand having at least one acrylamide functional group, thereby immobilizing an affinity ligand on a solid support.

In a particular embodiment, the ligand is selected from the group consisting of a nucleic acid, a modified nucleic acid and a nucleic acid analog. The steps of activating the latent thiol groups and reacting the activated thiol groups can occur essentially simultaneously. In alternate embodiments, the solid support is formed from glass, ceramic, plastic and metal. The solid support can comprise two or more spatially distinct regions, each region comprising a plurality of immobilized nucleic acids. The solid support can further comprises a polymer layer. The solid support can comprise a microarray.

In another aspect, the invention is directed to the product formed by the method of forming a solid support described above.

In another embodiment, the invention is directed to a method of immobilizing an affinity ligand on microarray comprising the steps of providing a solid support comprising immobilized latent thiol groups, activating the latent thiol groups, and reacting the activated thiol groups with an affinity ligand having at least one $\alpha,\beta$ unsaturated carbonyl functional group, thereby immobilizing an affinity ligand on a solid support. In a particular embodiment, the ligand is selected from the group consisting of a nucleic acid, a modified nucleic acid and a nucleic acid analog. The steps of activating the latent thiol groups and reacting the activated thiol groups can occur essentially simultaneously.

In another embodiment, the invention is directed to a method of immobilizing an affinity ligand on a microarray comprising the steps of providing a solid support comprising immobilized latent thiol groups, activating the latent thiol groups, and reacting the activated thiol groups with an affinity ligand having at least one $\alpha,\beta$ unsaturated carbonyl functional group, thereby immobilizing an affinity ligand on a solid support. In a particular embodiment, the ligand is a nucleic acid, a modified nucleic acid or a nucleic acid analog. The steps of activating the latent thiol groups and reacting the activated thiol groups can occur essentially simultaneously.

The method can additionally include contacting a glass solid support with a silane compound to form a solid support having an unsaturated aliphatic surface. The silane compound can be represented by Structural Formula I:

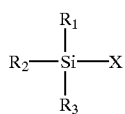

In Structural Formula I, X is a halogen, and $R_1$, $R_2$ and $R_3$ are each, independently, a halogen, an alkyl group, an alkenyl group or a group having at least one α,β-unsaturated carbonyl, provided that at least one of $R_1$, $R_2$ or $R_3$ is an alkenyl group or a group having at least one α,β-unsaturated carbonyl. The unsaturated aliphatic surface is then contacted with a polymerization solution containing free radical initiator, a disulfide bisacrylamide, and optionally containing an acrylamide to form a solid support comprising immobilized latent thiol groups. Disulfide bisacrylamides can be represented by Structural Formula IIA:

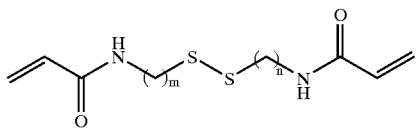

In Structural Formula IIA, n and m are each, independently, a positive integer.

The latent thiol groups can be activated by contacting the solid support with a disulfide reducing agent. When it is desirable to have a crosslinked gel having immobilized thiol groups, the polymerization solution can additionally include alkylene bisacrylamide.

In an alternative embodiment, the unsaturated aliphatic surface is then contacted with a polymerization solution containing free radical initiator, a compound having a α,β-unsaturated carbonyl and a protected thiol group, and optionally containing an acrylamide to form a solid support comprising immobilized latent thiol groups. The compound having an (α,β-unsaturated carbonyl and a protected thiol group preferably can be represented by Structural Formulas IIB–IID:

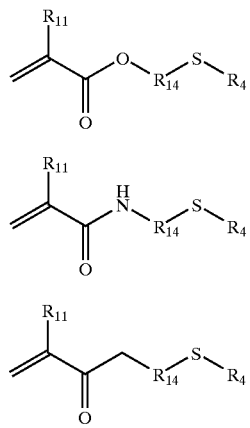

In Structural Formulas IIB–IID, $R_{11}$ and $R_4$ are defined as above. $R_{14}$ is —$(CH_2)_p$— or —$(OCH_2CH_2)_p$—. In a preferred embodiment, $R_4$ is —$SR_{15}$, where in $R_{15}$ is a substituted or unsubstituted alkyl group, a substituted or unsubstituted aromatic group or a substituted or unsubstituted aralkyl group.

In several embodiments of the invention, it is useful to provide latent thiol groups through the use of polymerizable disulfide compounds. As indicated in Structures IIB–D, such compounds can be monofunctional or bifunctional with regard to the α,β unsaturated carbonyl group. A commercially available example of a bifunctional disulfide reagent is BAC. An example of a monofunctional disulfide reagent is AEMA (Schnaar, R. L. et al., 1985, *Analytical Biochemistry*, 151:268–281). Additional monofunctional acrylamide disulfide derivatives can be generated by reacting BAC with the reducing agents β-mercaptoethanol and thioacetic acid, as shown if FIGS. 8 and 9.

In a particular embodiment, the free radical initiator is added to the polymerization solution after the solution is in contact with the unsaturated aliphatic surface of the solid support.

The method can additionally include derivatizing the solid support with a latent thiol group, thereby forming a solid support having immobilized latent thiol groups. In a particular embodiment, the solid support includes an amine functional group and the solid support is derivatized by contacting the solid support with a compound represented by Structural Formula III:

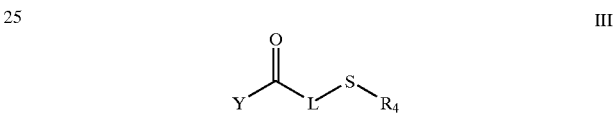

In Structural Formula III, Y is a leaving group, L is a linking group, and $R_4$ is a thiol protecting group. The derivatized solid support formed has immobilized latent thiol groups.

In a particular embodiment, Y is one of the following:

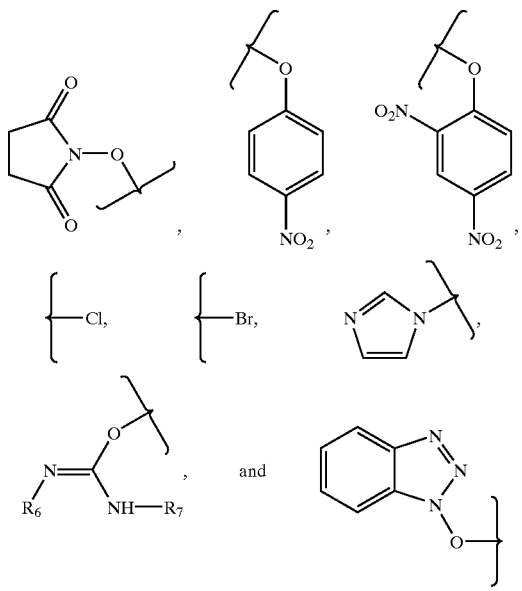

wherein $R_6$ and $R_7$ are each, independently, a substituted or unsubstituted alkyl group, a substituted or unsubstituted alkenyl group, a substituted or unsubstituted aromatic group, a substituted or unsubstituted heteroaromatic group, a substituted or unsubstituted aralkyl, or a substituted or unsubstituted heteroaralkyl group.

In a particular embodiment, $R_4$ is one of the following groups:

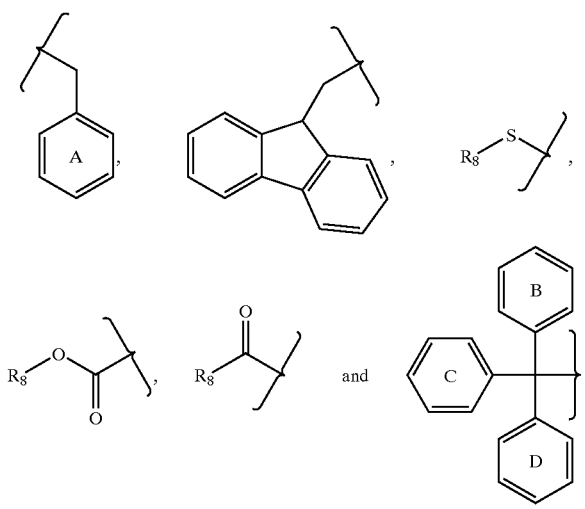

wherein R₈ is a substituted or unsubstituted alkyl group, a substituted or unsubstituted alkenyl group, a substituted or unsubstituted aromatic group, a substituted or unsubstituted heteroaromatic group, a substituted or unsubstituted aralkyl, or a substituted or unsubstituted heteroaralkyl group.

In another aspect, the invention is directed to a method of preparing a solid support having immobilized thiol groups. The method includes contacting a glass solid support with a silane compound represented by Structural Formula I to form a solid support having an unsaturated aliphatic surface. The unsaturated aliphatic surface of the solid support is then contacted with a polymerization solution containing free radical initiator, a disulfide bisacrylamide represented by Structural Formula IIA–D, and optionally containing an acrylamide to form a solid support comprising immobilized latent thiol groups. The latent thiol groups of the solid support are then contacted with a disulfide reducing agent to form a solid support having immobilized thiol groups.

In one embodiment, the solid support is doped or undoped silica, alumina, quartz or glass, and the method further comprises the steps of contacting the solid support with a compound comprising a silane group or a carboxylic acid and a substituted or unsubstituted alkenyl group or a group having at least one α,β-unsaturated carbonyl, thereby forming a solid support having an unsaturated aliphatic surface, and contacting the unsaturated aliphatic surface of the solid support with a polymerization solution containing free radical initiator, a disulfide bisacrylamide and optionally containing an acrylamide, wherein the disulfide bisacrylamide is represented by the following structural formula:

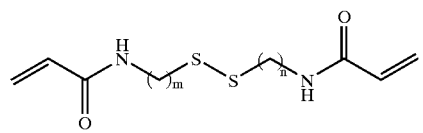

wherein n and m are each, independently, a positive integer, thereby forming a solid support comprising immobilized latent thiol groups.

The compound can be represented by the following structural formula:

$$R_2—\underset{\underset{R_3}{|}}{\overset{\overset{R_1}{|}}{Si}}—X$$

wherein X is a halogen, and $R_1$, $R_2$ and $R_3$ are each, independently, a halogen, a substituted or unsubstituted alkyl group, a substituted or unsubstituted alkenyl group or a group having at least one (α,β-unsaturated carbonyl, provided that at least one of $R_1$, $R_2$ or $R_3$ is a substituted or unsubstituted alkenyl group or a group having at least one α,β-unsaturated carbonyl.

The latent thiol groups can be activated by contacting the solid support with a disulfide reducing agent. The polymerization solution can further include alkylene bisacrylamide. The free radical initiator can be added to the polymerization solution after the solution is in contact with the unsaturated aliphatic surface of the solid support The solid support can be gold, silver, copper, cadmium, zinc, palladium, platinum, mercury, lead, iron, chromium, manganese, tungsten, and alloys thereof, and the method can further comprise the steps of contacting the solid support with a compound comprising a thiol group, sulfide or disulfide group and a substituted or unsubstituted alkenyl group or a group having at least one α,β-unsaturated carbonyl, thereby forming a solid support having an unsaturated aliphatic surface, and contacting the unsaturated aliphatic surface of the solid support with a polymerization solution containing free radical initiator, a disulfide bisacrylamide and optionally containing a comonomer, wherein the disulfide bisacrylamide is represented by the following structural formula:

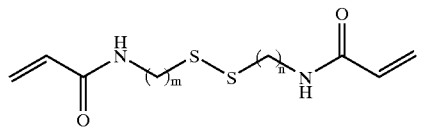

wherein n and m are each, independently, a positive integer, thereby forming a solid support comprising immobilized latent thiol groups.

The solid support can be platinum or palladium, and the method can further comprise the steps of contacting the solid support with a compound comprising a nitrile or isonitrile group and a substituted or unsubstituted alkenyl group or a group having at least one α,β-unsaturated carbonyl, thereby forming a solid support having an unsaturated aliphatic surface, and contacting the unsaturated aliphatic surface of the solid support with a polymerization solution containing free radical initiator, a disulfide bisacrylamide and optionally containing an acrylamide, wherein the disulfide bisacrylamide is represented by the following structural formula:

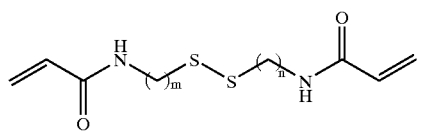

wherein n and m in are each, independently, a positive integer, thereby forming a solid support comprising immobilized latent thiol groups.

The solid support can be copper, and the method can further comprise the steps of contacting the solid support with a compound comprising a hydroxamic acid group and a substituted or unsubstituted alkenyl group or a group having at least one α,β-unsaturated carbonyl, thereby forming a solid support having an unsaturated aliphatic surface, and contacting the unsaturated aliphatic surface of the solid support with a polymerization solution containing free radical initiator and disulfide bisacrylamide and optionally containing an acrylamide, wherein the disulfide bisacrylamide is represented by the following structural formula:

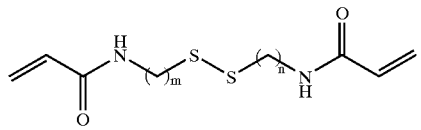

wherein n and m are each, independently, a positive integer, thereby forming a solid support comprising immobilized latent thiol groups.

The solid support can be a polymer comprising a reactive functional group, and the method can further comprise the steps of contacting the solid support with a compound comprising a functional group which can react to form a bond with the reactive functional group and a substituted or unsubstituted alkenyl group or a group having at least one α,β-unsaturated carbonyl, thereby forming a solid support having immobilized unsaturated aliphatic group, and contacting the unsaturated aliphatic groups of the solid support with a polymerization solution containing free radical initiator, a disulfide bisacrylamide and optionally containing an acrylamide, wherein the disulfide bisacrylamide is represented by the following structural formula:

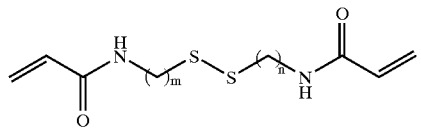

wherein n and m are each, independently, a positive integer, thereby forming a solid support comprising immobilized latent thiol groups.

The polymeric solid support can be polystyrene. The reactive functional group of the polymeric solid support can be an amine group or a hydroxyl group and the compound is represented by the following structural formula:

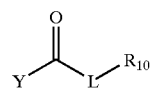

wherein Y is a leaving group, L is a linking group, and $R_{10}$ is a substituted or unsubstituted alkenyl group or a group having at least one α,β-unsaturated carbonyl. Y can be:

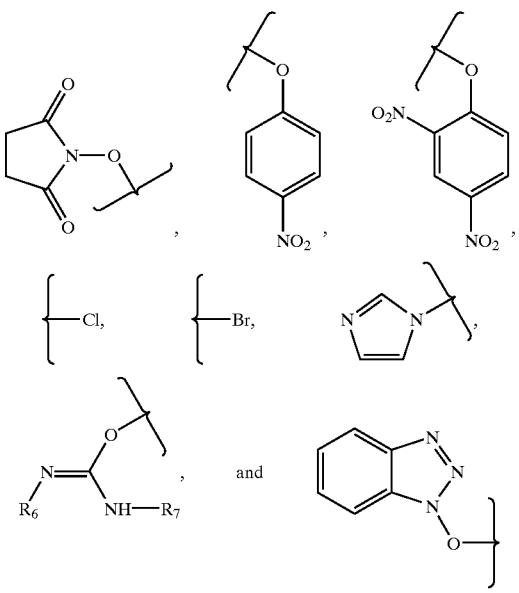

wherein $R_6$ and $R_7$ are each, independently, a substituted or unsubstituted alkyl group, a substituted or unsubstituted alkenyl group, a substituted or unsubstituted aromatic group, a substituted or unsubstituted heteroaromatic group, a substituted or unsubstituted aralkyl, or a substituted or unsubstituted heteroaralkyl group.

The method can further comprise the step of derivatizing a solid support with a latent thiol group, thereby forming a solid support having immobilized latent thiol groups. The solid support can be doped or undoped silica, alumina, quartz or glass, and the solid support can be derivatized by contacting it with a compound comprising a silane group or a carboxylic acid group and a latent thiol group.

The solid support can be platinum or palladium, and the solid support is derivatized by contacting it with a compound comprising a nitrile or isonitrile group and a latent thiol group.

The solid support can be a polymer comprising reactive functional groups, and the solid support is derivatized by contacting it with a compound comprising a functional group which can react to form a bond with the reactive functional group and a latent thiol group. The polymeric solid support can be polystyrene The reactive functional group of the polymeric solid support can be an amine or a hydroxyl group and the solid support can be derivatized by contacting the solid support with a compound represented by the following structural formula:

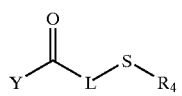

wherein Y is a leaving group, L is a linking group, and $R_4$ is a thiol protecting group, thereby forming a solid support having immobilized latent thiol groups. Y can be:

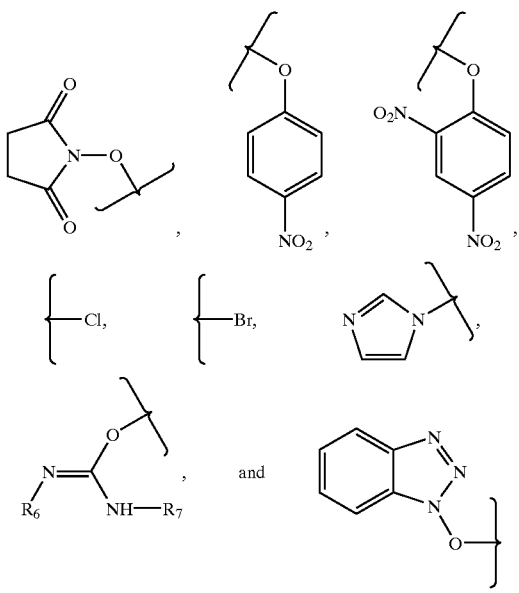

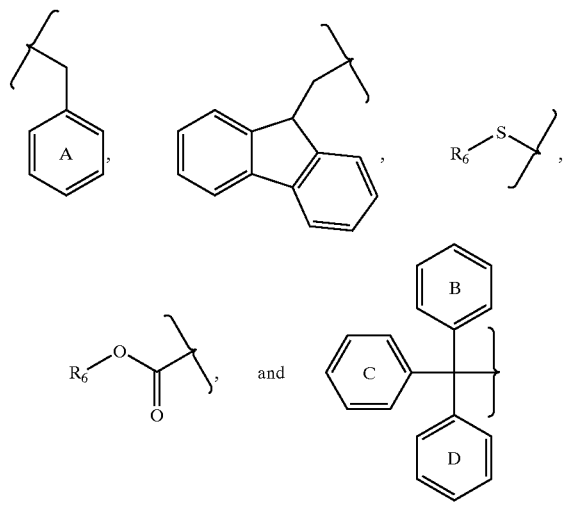

wherein $R_6$ and $R_7$ are each, independently, a substituted or unsubstituted alkyl group, a substituted or unsubstituted alkenyl group, a substituted or unsubstituted aromatic group, a substituted or unsubstituted heteroaromatic group, a substituted or unsubstituted aralkyl, or a substituted or unsubstituted heteroaralkyl group. $R_4$ can be:

wherein $R_6$ is a substituted or unsubstituted alkyl group, a substituted or unsubstituted alkenyl group, a substituted or unsubstituted aromatic group, a substituted or unsubstituted heteroaromatic group, a substituted or unsubstituted aralkyl, or a substituted or unsubstituted heteroaralkyl group.

In another embodiment, the invention is directed to a method of making a solid support having immobilized thiol groups, comprising the steps of contacting a glass solid support with a silane compound represented by the following structural formula:

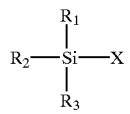

wherein X is a halogen, and $R_1$, $R_2$ and $R_3$ are each, independently, a halogen, an alkyl group, an alkenyl group or a group having at least one α,β-unsaturated carbonyl, provided that at least one of $R_1$, $R_2$ or $R_3$ is an alkenyl group or a group having at least one (α,β-unsaturated carbonyl, thereby forming a solid support having an unsaturated aliphatic surface, contacting the unsaturated aliphatic surface of the solid support with a polymerization solution containing free radical initiator, a disulfide bisacrylamide and optionally containing an acrylamide, wherein the disulfide bisacrylamide is represented by the following structural formula:

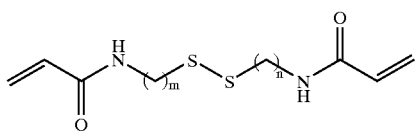

wherein n and m are each, independently, a positive integer, thereby forming a solid support comprising immobilized latent thiol groups, and contacting the latent thiol groups with a disulfide reducing agent, thereby forming a solid support having immobilized thiol groups.

In another embodiment, the invention is directed to a method of forming an array of nucleic acids inmmobilized on a solid support including forming an amine-derivatized region on the support, treating the amine-derivatized region with a thiolating agent such that latent thiol groups immobilized on the support are formed, activating the latent thiol groups, contacting the activated thiol groups with a plurality of nucleic acids comprising acrylamide functional groups, and forming a covalent bond between the two groups, thereby forming an array of nucleic acids immobilized on the solid support. In alternate embodiments, each nucleic acid contained in the array includes a nucleotide sequence identical to or substantially identical to, the nucleotide sequence of the other nucleic acids of the array, or nucleic acids with a plurality of nucleotide sequences are contained in the array. The solid support can include a plurality of amine-derivatized regions. The method can further include a step of blocking any unbonded reactive thiol groups remaining following the binding of the nucleic acids to the thiol groups.

In another aspect, the invention is directed to a kit for attaching nucleic acids to a solid support including a solid support component including a plurality of immobilized latent thiol groups and instructions for activating the thiol groups to form covalent bonds with nucleic acids including acrylamide functional groups. Such kits can also include an activator component, an acrylamide functional nucleic acids component, a blocking component and/or a wash buffer.

In an alternate embodiment, the invention is directed to a kit for attaching nucleic acids to a solid support including a solid support component including a plurality of immobilized latent thiol groups and nucleic acids including acrylamide functional groups. In a particular embodiment, the nucleic acids are immobilized on the solid support by a covalent bond between the immobilized thiol groups and the nucleic acids. Such kits can also include an activator component, a blocking component and/or a wash buffer.

In another aspect, the invention is directed to a method for detecting or separating target nucleic acids from other components contained in a sample including providing a solid support comprising a plurality of immobilized nucleic acids comprising nucleotide sequences complementary to a subsequence of the nucleotide sequence of the target nucleic acid, wherein the nucleic acids are immobilized by a covalent bond formed between a thiol group immobilized on the solid support and an acrylamide functional group contained on the nucleic acid, contacting the immobilized nucleic acid with the test sample, and hybridizing target nucleic acids to immobilized nucleic acids with complementary subsequences, thereby separating target nucleic acids from other components contained in the sample. After detection or separation, the target nucleic acids can be amplified. The method can be used in an assay for detecting a contaminant in a sample, for medical diagnosis of a medical condition, for genetic and physical mapping of genomes, for monitoring gene expression and for DNA sequencing.

In another embodiment, the invention is directed to a method for detecting or separating target nucleic acids from other components contained in a sample including providing a solid support comprising a plurality of immobilized thiol groups, contacting the thiol groups with a plurality of nucleic acids comprising nucleotide sequences complementary to a subsequence of the nucleotide sequence of the target nucleic acid and acrylamide functional groups, forming a covalent bond between the two groups, thereby immobilizing the nucleic acids on the solid support, contacting the immobilized nucleic acids with the test sample, and hybridizing target nucleic acids to immobilized nucleic acids with complementary subsequences, thereby detecting or separating target nucleic acids from other components contained in the sample. After detection or separation, the target nucleic acids can be amplified. The method can be used in an assay for detecting a contaminant in a sample, for medical diagnosis of a medical condition, for genetic and physical mapping of genomes, for monitoring gene expression and for DNA sequencing.

DETAILED DESCRIPTION OF THE INVENTION

Figure 1:
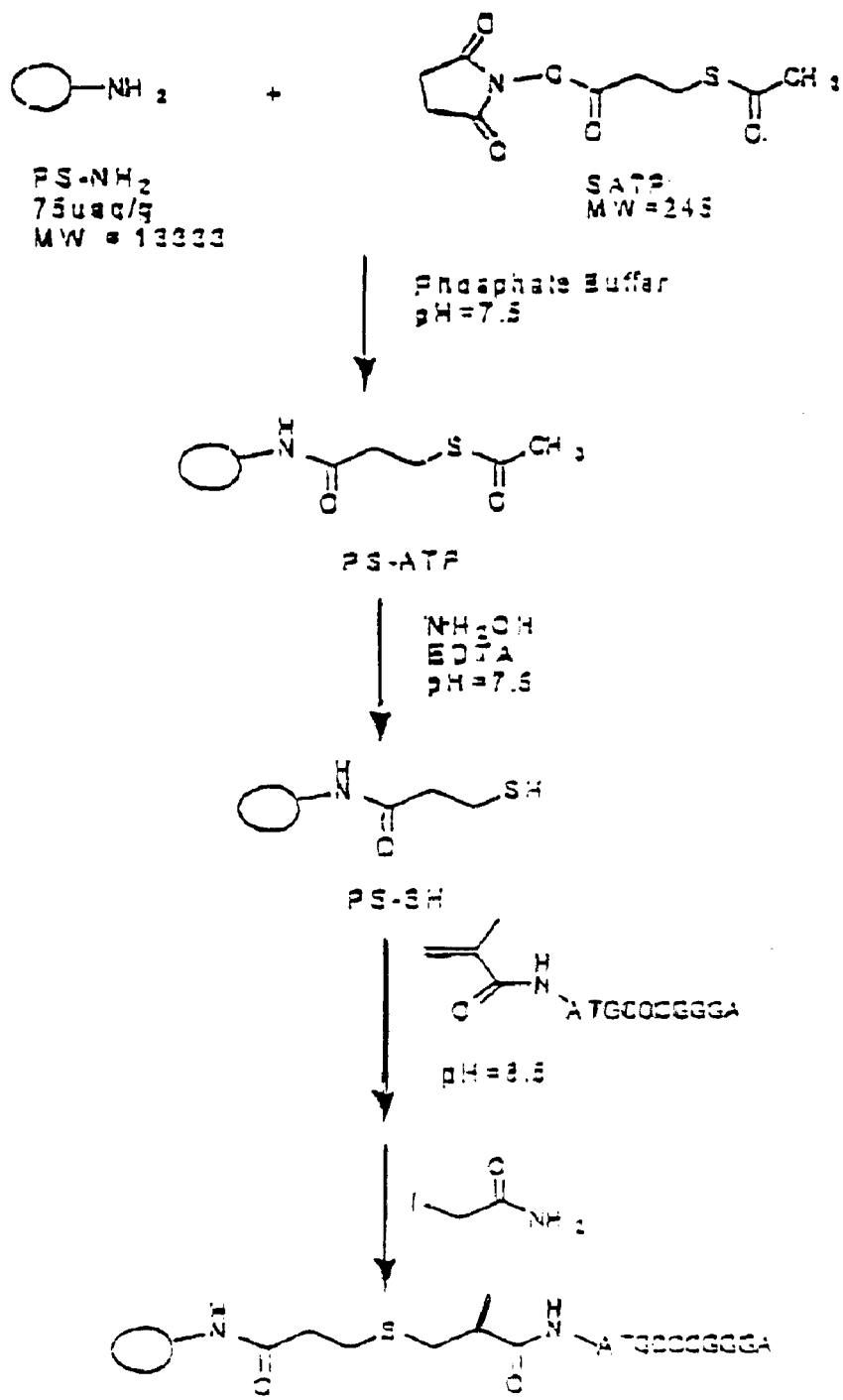
FIG. 1 is a schematic representation of a method of derivatizing an amine group bearing polystyrene support with an acrylamide derivatized oligonucleotide.

The present invention is based, at least in part, on the discovery of a novel and convenient method of immobilizing an affinity ligand on a solid support. The method utilizes a covalent bond formed between a thiol group immobilized on the solid support and an acrylamide functional group contained on an affinity ligand to immobilize the affinity ligand to the support. In a particular embodiment, the covalent bond formed is a sulfide, a thioether, bond.

The method and the supports it produces are advantageous in several respects. The method utilizes reagents which are both readily available and compatible with the types of analysis conducted with solid supports. Because the materials can be used in aqueous solutions, the need for special skills and sophisticated chemical apparatus are minimized. In addition, because the materials and the supports they form are quite stable, the reproducibility from support to support which has previously proved so difficult to achieve can be realized. This stability also permits the components forming the bond to be combined at different times. For example, because solid supports containing the latent thiol groups of the invention are extremely stable, they can be produced under consistent conditions for use at a later time. Prior to analysis, the latent thiol groups can be activated and contacted with the acrylamide modified nucleic acids to form a support containing immobilized nucleic acids. In a particular embodiment, the thiol groups are activated by contact with a reducing agent.

In one embodiment, the method is directed to a method of immobilizing an affinity ligand on a solid support. The method includes providing a solid support comprising an immobilized thiol group, contacting the thiol group with an affinity ligand comprising an acrylamide functional group, and forming a covalent bond between the two groups, thereby immoblizing the affinity ligand on the solid support.

The term "affinity ligand" is intended to include any molecule that can form a specific binding complex with a target analyte and can be immobilized on a suitable solid support. Any suitable ligand can be used in the present invention provided that it can form a specific binding complex with a target analyte. Methods for determining the thermal stability of binding complexes and, in particular, hybridization complexes are well known in the literature. Wetmur, *Critical Reviews in Biochemistry and Molecular Biology*, 26:227–259 (1991); Quartin and Wetmur, *Biochemistry*, 28:1040–1047 (1989).

One especially useful example of an affinity ligand is a single-stranded nucleic acid, which can bind by hybridization, for example, to an analyte that contains a complementary nucleic acid sequence. The single stranded nucleic acid affinity ligand can be complementary to the entire analyte nucleic acid sequence or to a portion thereof. Single-stranded nucleic acids can also be used for isolation of duplex nucleic acids by triplex formation (Hogan and Kessler, U.S. Pat. No. 5,176,966 and Cantor, et al., U.S. Pat. No. 5,482,836, the teachings of which are incorporated herein by reference). Double-stranded nucleic acids can also serve as useful affinity ligands for nucleic acid binding proteins, or for nucleic acid analytes that bind to the ligand by triplex or tetraplex formation. The conditions under which a single stranded nucleic acid will bind to another nucleic acid to be immobilized on a solid support can be estimated by those skilled in the art using the procedure referenced above. In addition, the melting temperature ($T_m$) of the two nucleic acids provides a reasonable framework for estimating the temperate at which an nucleic acid analyte will hybridize to a nucleic acid affinity ligand. In general, the $T_d$ is lower than the $T_m$ by about 15 to 25° C. and, therefore, the temperature at which the gel should be run to facilitate specific hybridization between the analyte and affinity ligand should be about 15 to 25° C. or more below the $T_m$.

Nucleic acid aptamers (Tuerk and Gold, *Science* (1990) 249:5050; Joyce, *Gene* (1989), 82:83–87; Ellington and Szostak, *Nature* (1990), 346:818–822) can also be used as affinity ligands in the process of the present invention. Aptamers can be selected against many kinds of analytes, including proteins, small organic molecules, and carbohydrates (reviewed in Klug and Famulok, *Molecular Biology Reports* (1994), 20:97–107). Thus, selection of aptamer ligands offers a simple and flexible mechanism for obtaining affinity ligands against virtually any target molecule.

Other useful ligands include proteins or polypeptides which can bind to specific analytes. An especially useful class of protein ligands are antibody molecules, which can be elicited against a wide range of analytes by immunization methods. Antibodies ligands can be monoclonal or polyclonal. In addition, a fragment of an antibody can be an affinity ligand. Similarly, receptor proteins may be useful as ligands for purification and detection of analytes that bind to or are bound by them.

Carbohydrates have been successfully used as affinity ligands for electrophoretic purification of lectins (Horejsi and Kocourek, *Biochim. Biophys. Acta* 5(1974), 336:338–343), and may be useful for purification and detection of molecules that bind to specific carbohydrates or glycoproteins.

Binding or non-binding conditions of proteins, aptamers and lectins for specific ligands can be estimated using the procedure outlined above for estimating the stability of analyte/affinity ligand complexes. In addition, equilibrium dialysis experiments can provide a rational method of predicting the stability of analyte/affinity ligand complexes. For example, the dissociation constant of a protein for a particular ligand can be determined in the electrophoresis buffer at several different pHs, temperatures or ionic strengths. The higher the dissociation constant, the weaker the binding between the protein and the ligand (see Segel, I. H., *Biochemical Calculations*, $2^{nd}$ Edition (1976), John Wiley & Sons, N.Y., p. 241–244). From this data a binding and a non-binding condition can be estimated.

Many other types of immobilized ligands are possible including peptides, amino acids, nucleosides, small organic molecules, lipids, hormones, drugs, enzyme substrates, enzyme inhibitors, enzymes, coenzymes, inorganic molecules, chelating agents, macromolecular complexes, polysaccharides, monosaccharides, and others.

In a particular embodiment, a nucleic acid can be utilized as an affinity ligand. Such nucleic acids include deoxyribonucleic acid (hereinafter "DNA"), or ribonucleic acid (hereinafter "RNA"), modified nucleic acids, nucleic acid analogs, and chimeric molecules of a mixed class comprising a nucleic acid with another organic component, e.g., peptide nucleic acids. Nucleic acids can be single-stranded or double-stranded nucleic acids. Typically, the length of a nucleic acid will be at least about 5 nucleotides in length, more typically between about 5 and 100 nucleotides even more typically between 5 and 50, although it can be as long as several thousand bases.

Such nucleic acids are typically "isolated" nucleic acids, e.g., nucleic acids separated away from the components of their source of origin (e.g., as it exists in cells, or in a mixture such as a library) and can have undergone further processing. Isolated nucleic acids include nucleic acids obtained by methods known to those of skill in the art. These isolated nucleic acids include substantially pure nucleic acids, e.g., nucleic acids free from protein, carbohydrate or lipids. Nucleic acids can be produced by chemical synthesis, or by combinations of biological and chemical methods or by recombinant methods.

The term "modified nucleic acid" is intended to include nucleic acids containing modified bases, deoxyribose groups or phosphates. Examples of nucleic acids having modified bases, include, for example, acetylated, carboxylated or methylated bases e.g., 4-acetylcytidine, 5-carboxymethylaminomethyluridine, 1-methylinosine, norvaline or allo-isoleucine.

The term "nucleic acid analog" is intended to include molecules that lack a conventional deoxyribose/ribose-phosphodiester backbone, but which retain the ability to form Watson-Crick type base pairs with complementary single-stranded nucleic acids. Examples of nucleic acid analogues include peptide nucleic acids (PNAS; Eghohm et al., 1992, *J. Am. Chem. Soc.* 114: 1895–1897) and morpholino oligomers (morpholinos; Summerton and Weller, *Antisense Nucleic Acid Drug Dev.*, (1997) 7:187–195). It will be apparent to those skilled in the art that similar design strategies can be used to construct other nucleic acid analogs that will have useful properties for immobilized probe assays.

The term "alkyl group", as used herein, is intended to include straight chained or branched $C_1$–$C_{18}$ hydrocarbons which are completely saturated, or cyclic $C_3$–$C_{18}$, hydrocarbons which are completely saturated. Lower alkyl groups are straight chained or branched $C_1$–$C_8$ hydrocarbons or $C_3$–$C_8$ cyclic hydrocarbons which are completely saturated. Alkyl groups are preferably lower alkyl groups.

The term "alkenyl group," as used herein, is intended to include straight chained or branched $C_1$–$C_{18}$ hydrocarbons which have one or more double bond, or cyclic $C_3$–$C_{18}$ hydrocarbons which have one or more unconjugated double bond. Lower alkenyl groups are straight chained or branched $C_1$–$C_8$ hydrocarbons which have one or more double bond or $C_3$–$C_8$ cyclic hydrocarbons which have one or more unconjugated double bond. Alkenyl groups are preferably lower alkenyl groups.

The term "aromatic group" is intended to include carbocyclic aromatic ring systems (e.g., phenyl) and carbocyclic aromatic ring systems fused to one or more carbocyclic aromatic or non-aromatic ring (e.g., naphthyl, anthracenyl and 1,2,3,4-tetrahydronaphthyl).

Heteroaromatic groups, as used herein, include heteroaryl ring systems (e.g., thienyl, pyridyl, pyrazole, isoxazolyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, or oxadiazoles) and heteroaryl ring systems in which a carbocyclic aromatic ring, carbocyclic non-aromatic ring, heteroaryl ring or a heterocycloalkyl ring is fused to one or more other heteroaryl rings (e.g., benzo(b)thienyl, benzimidazole, indole, tetrahydroindole, azaindole, indazole, quinoline, imidazopyridine, purine, pyrrolo[2,3-d]pyrimidine, and pyrazolo[3,4-d]pyrimidine).

The term "aralkyl group," as used herein, is intended to include aromatic substituents that are linked to a moiety by an alkyl group that preferably has from one to about six carbon atoms.

The term "heteroaralkyl group," as used herein, is intended to include heteroaromatic substituents that are linked to a moiety by an alkyl group that preferably has from one to about six carbon atoms.

The term "heterocycloalkyl group," as used herein, is intended to include non-aromatic ring systems that preferably has 5 to 6 atoms and include at least one heteroatom, such as nitrogen, oxygen, or sulfur. Examples of heterocycloalkyl groups include morpholines, piperidines, and piperazines.

Suitable substituents for aliphatic groups, aromatic groups, aralkyl groups, heteroaromatic groups and heterocycloalkyl groups include aromatic groups, halogenated aromatic groups, lower alkyl groups, halogenated lower alkyl (e.g. trifluoromethyl and trichloromethyl), —O-(aliphatic group or substituted aliphatic group), —O-(aromatic group or substituted aromatic group), benzyl, substituted benzyl, halogens, cyano, nitro, —S-(aliphatic or substituted aliphatic group), and —S-(aromatic or substituted aromatic).

The term "linking group," as used herein, includes substituted or substituted alkyl groups, substituted or unsubstituted aromatic groups, substituted or unsubstituted aralkyl groups and substituted or unsubstituted polyether groups.

The affinity ligands of the invention comprise a α,β-unsaturated carbonyl group. A preferred α,β-unsaturated carbonyl group is an acrylamide. The term "acrylamide" is intended to include compounds represented by Structural Formula IV:

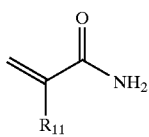

IV

In Structural Formula IV, $R_{11}$ is —H, or a substituted or unsubstituted alkyl group. In a preferred embodiment, $R_{11}$ is a —H or a methyl group.

An affinity ligand can be derivatized with a selectively thiol reactive group. Such thiol reactive groups can include methacrylate, methacrylamide, (α,β unsaturated carbonyl groups [CH2CHC(F2)], α,β unsaturated difluoro groups and maleimide groups. In general, such groups show enhanced reactivity with thiol groups, as opposed to other functional groups present in the reaction.

Figure 8:
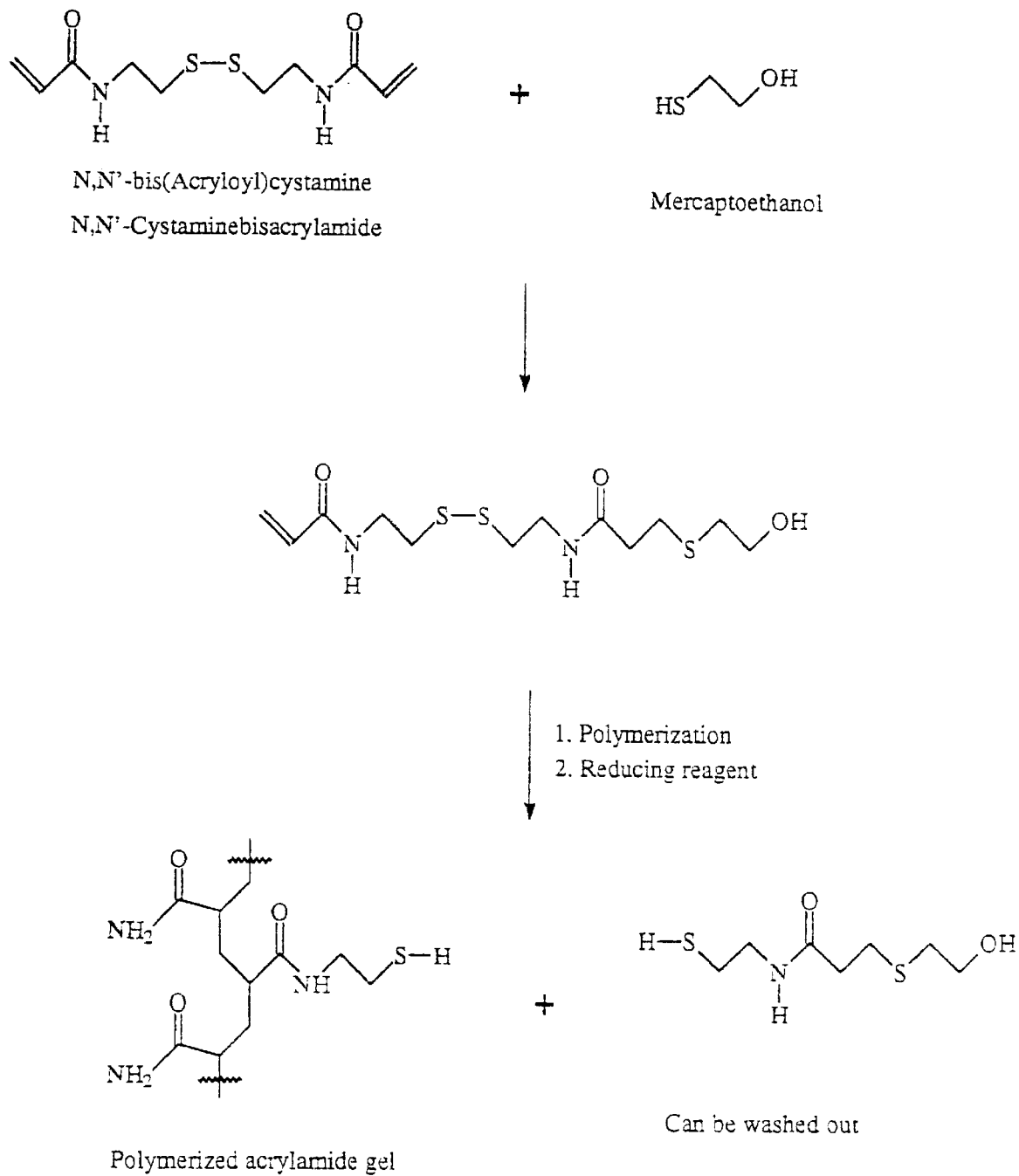
FIG. 8 is a schematic of a synthesis for a non-symmetrical disulfide acrylamide.
Figure 9:
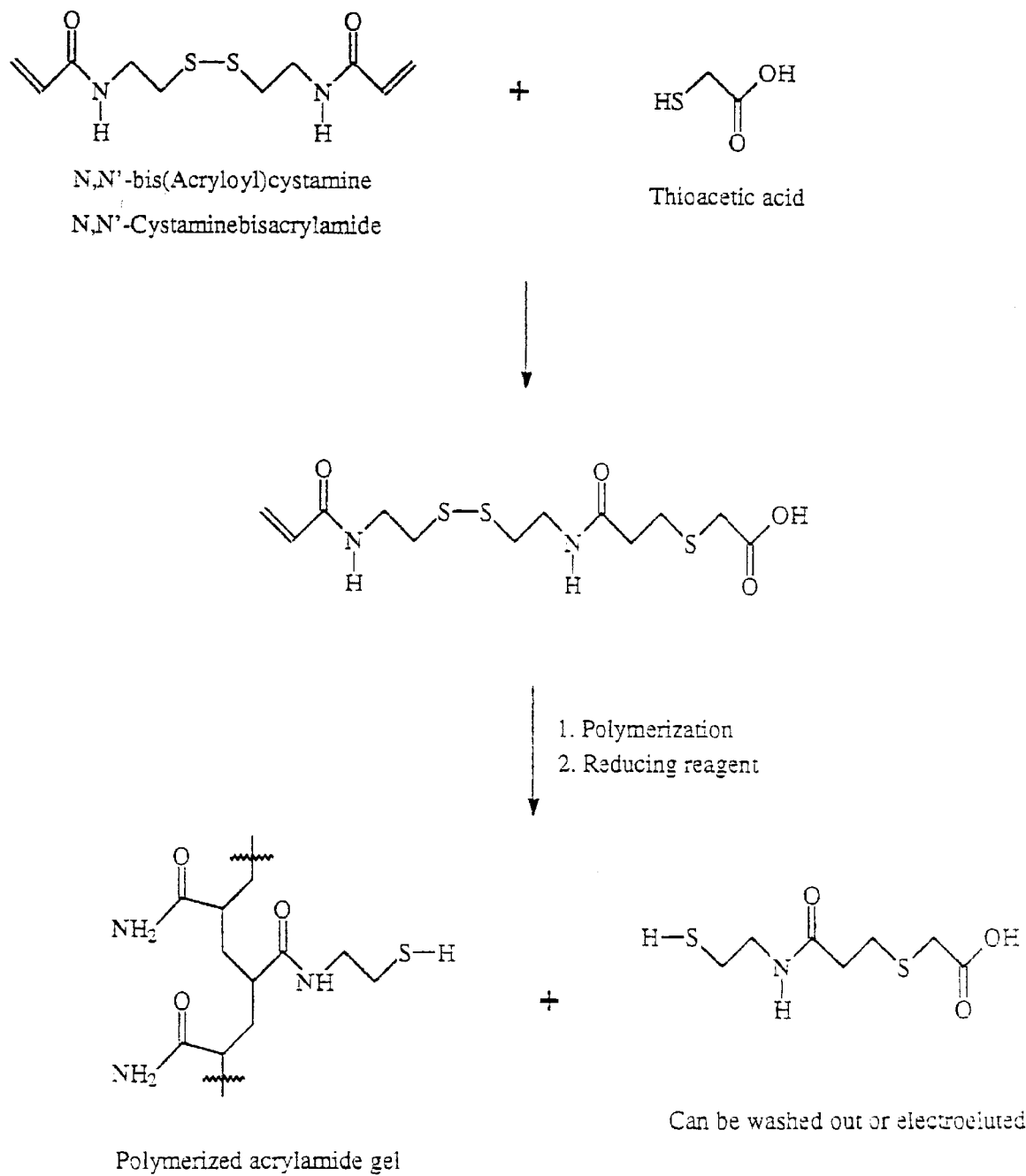
FIG. 9 is a schematic of a synthesis for a non-symmetrical disulfide acrylamide.

In several embodiments of the invention, it is useful to provide latent thiol groups through the use of polymerizable disulfide compounds. As indicated in Structures IIB–D, such compounds can be monofunctional or bifunctional with regard to the α,β unsaturated carbonyl group. A commercially available example of a bifunctional disulfide reagent is BAC. An example of a monofunctional disulfide reagent is AEMA (Schnaar, R. L. et al., 1985, *Analytical Biochemistry*, 151:268–281). Additional monofunctional acrylamide disulfide derivatives can be generated by reacting BAC with the reducing agents β-mercaptoethanol and thioacetic acid, as shown if FIGS. 8 and 9.

The term "acrylamide group" is intended to include those groups which are represented by Structural Formula V:

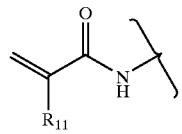

V

In Structural Formula V, $R_{11}$ is defined as in Structural Formula IV. "}" represents the point of attachment of the affinity ligand. Methods for derivatizing nucleic acid affinity ligands with an acrylamide group can be found in Boles, et al., U.S. Pat. No. 5,932,711 and Hoffman and Dong, U.S. Pat. No. 5,034,428, the entire teachings of which are incorporated herein by reference.

A peptide or protein can be derivatized with an acrylamide group by reacting an amine group with an acrylic acid in the presence of a coupling agent such as dicyclohexylcarbodiimide or diisopropylcarbodiimide. The amine group of the peptide or protein can react with the acrylic acid to form an acrylamide group represented by Structural Formula V. Methods for coupling peptide or protein amine groups with carboxylic acid group, such as the carboxylic acid group of an acrylic acid, can be found in Stewart and Young, *Solid Phase Peptide Synthesis*, 2nd Edition, Pierce Chemical Company, Rockford, Ill., the entire teachings of which are hereby incorporated by reference.

Carbohydrates, antigens or drug molecules which have an amine group can also be coupled with acrylic acid to form an acrylamide group using a coupling agent such as dicyclohexylcarbodiimide or diisopropylcarbodiimide. Alternatively, the carboxylic acid group of acrylic acid can be converted into an active ester, such as a p-nitrophenol acrylate, a o,p-dinitrophenol acrylate, or N-hydroxysuccinamide acrylate, and then allowed to react with an amine group of a carbohydrate, antigen or drug molecule.

A thiol group is a group of the formula —SH. The term "latent thiol group" is intended to include thiol groups which have been protected with a thiol protecting group and disulfide groups of a polymer matrix. The term "thiol protecting group" is intended to include groups which can react with a thiol group causing the thiol group to be unreactive and which can be removed to regenerate the thiol group. Thiol protecting groups are known to those skilled in the art. For examples of thiol protecting groups see Greene, et al., *Protective Groups in Organic Synthesis* (1991), John Wiley & Sons, Inc., pages 277–308, the teachings of which are incorporated herein by reference in their entirety. In one embodiment, thiol protecting groups can include the following groups:

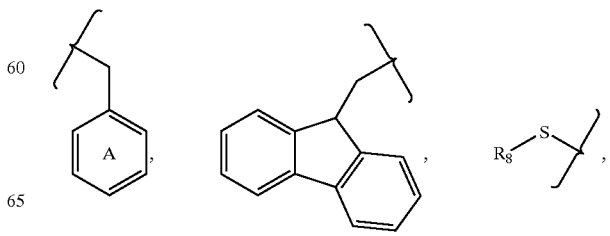

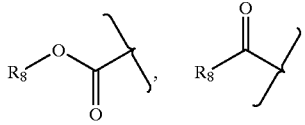 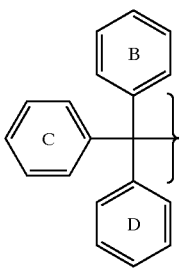

The term "Acrydite™ phosphoramidite" as used herein refers to the proprietary rylamide phosphoramidite sold by Mosaic Technologies, Waltham, Mass. This product allows addition of an acrylamide group directly to a DNA or an RNA oligonucleotide using standard beta-cyanoethylphosphoramidite methods.

The acronym "AEMA" is intended to encompass the compound known as 4-[[1-Oxo-3-[[2-[(1-oxo-2-propenyl)-amino]ethyl]dithio]propyl]amino]butanoic acid which as obtained from Ronald L. Schnaar, Department of Pharmacology and Neuroscience, he Johns Hopkins University School of Medicine, Baltimore, Md. (Schnarr, R. L. et aL, 1985 *Analytical Biochemistry* 151:268–281).

The acronym "APS" is intended to encompass an ammonium persulfate such as hat available from BioRad Laboratories, Inc., Hercules, Calif.

The term "acrylate slide" is intended to encompass a slide, e.g, a glass microscope slide, coated with an organosilane compound that includes an acrylamide or acrylic ester functionality. Such slides can be generated by treatment with (3'-acryloxypropyl)trimethoxysilane or other similar compounds available commercially, for example, from Gelest, Tullytown, Pa. Such slides can also be commercially obtained for example, from CEL Associates, Inc., Houston Tex, (see Cat. #ACR-25C).

The acronym "BAC" is intended to encompass the compound known as N,N'-bis(acryloyl)cystamine available, for example, from Fluka; Buchs, Switzerland.

The acronym "DMA" is intended to encompass the compound known as dimethylacrylamide.

The acronym "DMSO" is intended to encompass the compound known as dimethyl sulfoxide.

The acronym "DTNB" is intended to encompass the compound known as 5,5'-dithio-bis-(2-nitrobenzoic) acid.

The acronym "HEMA" is intended to encompass the compound known as 2-hydroxymethacrylate.

The acronym "ME" is intended to encompass compounds known as mercaptoethanol.

The acronym "P400mm" is intended to encompass compounds known as pol(yethylene glycol) 400 monomethyl ether monomethacrylate.

The acronym "SATP is intended to encompass the compound known as N-succinimidyl S-acetylthiopropionate available, for example, from Pierce; Rockford, Ill.

The acronym "SBB" is intended to encompass sodium borate buffers.

The acronym "SDS" is intended to encompass the compound known as sodium dodecyl sulfate.

The acronym "SSPE" is intended to encompass standard saline phosphate EDTA buffers.

The acronym "TAA" is intended to encompass thioacetic acids.

The acronym "TCEP" is intended to encompass the compound known as tris(2-carboxyethyl) phosphine hydrochloride.

The term "TE buffer" is intended to encompass a 10 mM Tris-HCl pH 8.3; 1 mM EDTA buffer.

The acronym "TEMED" is intended to encompass compounds known as N,N,N',N'-tetra-methyl-ethylenediamine available, for example, from BioRad Laboratories, Inc., Hercules, The term "GMS spotter" is intended to include a "GMS 417 Arrayer" (Affymetrix; Santa Clara, Calif.).

In a preferred embodiment, the thiol protecting group is a disulfide group. Disulfide protecting groups can be removed by treating with a disulfide reducing agent which reduces the disulfide bond to form two thiol groups. Disulfide reducing agents include compounds such as tris(2-carboxyethyl) phosphine hydrochloride (TCEP), β-mercaptoethanol and dithiothreitol.

A solid support having immobilized thiol groups is contacted with an affinity ligand of the invention, which has been derivatized with an acrylamide group. The thiol groups can react with the acrylamide group of the affinity ligand to form a covalent bond via a Michael condensation reaction to form a solid support having immobilized affinity ligands. Therefore, although the term "immobilized" when used in reference to other methods can encompass various means of attachment to a solid support including both ionic and covalent types of bonding, when used in reference to the present invention "immobilized" refers to attachment with a covalent bond.

The solid supports of the invention can be formed from a variety of materials including paper, glass, silica, metals, ceramics, plastic and polymers. Polymers can be cross-linked to form gels, e.g., electrophoretic gels, e.g., acrylamide gels. The solid supports can be of any shape or dimension. Porous filters, woven materials and meshes, planar sheets, microparticles, fibers, rods, optical fibers, dipsticks, beads, tubes, multiwell plates, cups and capillaries can all be used as solid supports.

In a preferred embodiment, the solid support of the invention is formed of glass, silica, metal, ceramic or a polymer such as polystyrene, crosslinked polystyrene, polyethylene, polypropylene, polymethacrylate, dextran and agarose and a polymer layer is applied to a surface of the solid support. In particularly preferred embodiments, the solid support is formed of glass and a polymer layer is applied to a surface of the solid support. In a particularly preferred embodiment, the solid support is planar in form and contains a polymer layer applied to a surface.

A preferred embodiment when the solid support is a chromatography bead, e.g., a polyacrylamide bead, is the use of BAC to form the thiol groups.

In one embodiment, an aliphatic group having a substituted or unsubstituted alkenyl group or a (α,β-unsaturated carbonyl group is attached to a surface by contacting the surface with an aliphatic group which has been derivatized with a group that can bind to the surface, thereby forming an unsaturated aliphatic surface. Therefore, selection of a functional group with which the aliphatic group is to be derivatized is dependent on the type of material to which the aliphatic group is to be attached. When the surface to which the aliphatic group is to be attached is doped or undoped silica, alumina, quartz or glass, the aliphatic group is preferably derivatized with a silane group or carboxylic acid. In on embodiment, when the aliphatic group is derivatized with a silane group, the compound can be represented by Structural Formula I.

In one embodiment, a glass or silica support is treated with an appropriate organosilane compound to provide a surface layer comprising a plurality of alpha-beta unsaturated groups. Preferred silanes include alkoxysilanes and chlorosilanes having vinyl, allylic, acrylamide, methacrylamide or acrylic ester functionalities. One preferred silane is (3'-acryloxpropyl)trimethoxysilane. This and other preferred silanes are commercially available from, for example, Gelest (Tullytown, Pa.).

When the aliphatic group is to be attached to a surface which is gold, silver, copper, cadmium, zinc, palladium, platinum, mercury, lead, iron, chromium, manganese, tungsten, or any alloys of the above metals, the aliphatic group to be attached is preferably derivatized with a thiol, sulfide or disulfide group. When the surface to which the aliphatic group is to be attached is platinum or palladium, the aliphatic group is preferably derivatized with a nitrile or isonitrile group. Finally, when the surface to which the aliphatic group is to be attached is copper, the aliphatic group is preferably derivatized with a hydroxamic acid group.

An acrylamide gel having latent thiol groups can be formed on the unsaturated aliphatic surface of the solid support by contacting the unsaturated aliphatic surface with a polymerization solution containing a free radical initiator, a disulfide bisacrylamide and optionally containing an acrylamide. Conditions for free radical polymerization of disulfide bisacrylamide monomers are similar to those used for polymerization of acrylamide monomers (for example, see Perbal, *A Practical Guide to Molecular Cloning*, 2nd Edition, (1988), John Wiley & Sons, New York, pages 15–17) and are further described in Example 5 and Example 7. Typically, the polymerization solution contains a disulfide bisacrylamide in about 0.1% to about 20% in an aqueous solution. If an acrylamide and/or a bisalkylene acrylamide is also present, the concentration of the disulfide bisacrylamide and the acrylamide and/or the bisalkylene acrylamide together is about 0.1% to about 20%. Optionally, an organic solvent, such as DMF, can be used to improve reactivity and/or solubility. The polymerization reaction is initiated by a free radical initiator. A free radical initiator is a substance which decomposes to form a free radical. Typical free radical initiators include ammonium persulfate, peroxides, and azo compounds such as azobisisobytyronitrile. Ammonium persulfate is a preferred free radical initiator. About 0.1% (weight/volume) to about 10% (weight/volume) of the free radical initiator is added to the polymerization solution either before the solution is in contact with the unsaturated aliphatic surface or after the polymerization solution is in contact with the unsaturated aliphatic surface.

Polymerization of the disulfide bisacrylamide on the surface of the solid support forms a solid support having immobilized disulfide groups which are latent thiol groups. The immobilized latent thiol groups can be converted to immobilized thiol groups by contacting the solid support with a disulfide reducing agent such as tris(2-carboxyethyl) phosphine hydrochloride (TCEP), β-mercaptoethanol and dithiothreitol.

Comonomers can be added to the BAC for co-polymerization. Useful comonomers include for example, acrylamide, bis acrylamide; N,N-dimethyl acrylamide, N-octyl acrylamide, poly(ethylene glycol) (n) dimethacrylate, n 200 or 400, (Catalog #00096 and 02364 (1998–2000 "Polymers and Monomers" Catalog, Polysciences, Inc, Warrington Pa.)). A preferred comonomer is pol(yethylene glycol) 400 monomethyl ether monomethacrylate (P400mm, Catalog #16665 (1998–2000 "Polymers and Monomers" Catalog, Polysciences, Inc, Warrington Pa.)).

Other comonomers that could be used are well known to those practiced in the art of polymer science and coatings; (see, e.g, 1998–2000 "Polymers and Monomers" Catalog, Polysciences, Inc, Warrington Pa.) In addition, it is well known that mixtures of three or more comonomers can be mixed to achieve polymers with desired properties. Comonomers can be added in organic solvents. Optionally, an organic solvent, such as DMF can be used improve reactivity and/or solubility.

In an alternate embodiment, a solution of acrylamide and non-symmetrical disulfide acrylamides are prepared together with a crosslinking compound such as bisacrylamide. The mixture is polymerized using ammonium persulfate with TEMED, ultraviolet (UV) light, heat, ionizing radiation or an equivalent known to those of skill in the art. The disulfide bonds are reduced, for example, using TCEP or a thiol exchange reaction with DTT. Thin polymer layers can be produced by dipping slides in a polymerizing solution. Thicker gels can be formed between glass plates.

In another embodiment, the solid support is a polymer which has reactive functional groups. Reactive functional groups include amines, amides, hydroxyl, carboxylic acid, and halogens. A preferred polymeric solid support is a polystyrene which has reactive functional groups. Preferred reactive functional groups are amine and hydroxyl groups. The solid support is contacted with a compound which has a functional group which can react with the reactive functional group of the polymer to form a double bond and a substituted or unsubstituted alkenyl or at least one α,β-unsaturated carbonyl to form a solid support having unsaturated aliphatic groups. When the reactive functional group is a halogen, it can react, for example, with an amine or an alkoxide to form a covalent bond. When the reactive functional group is a carboxylic acid, it can react, for example, with an amine or a hydroxide in the presence of dicyclohexylcarbodiimide. When the reactive functional group is an amine or a hydroxyl group, it can react, for example, with an ester, a carboxylic acid or a halogen to form a covalent bond. In a preferred embodiment when the solid support has an amine or a hydroxyl reactive group, it is contacted with a compound is represented by Structural Formula VI:

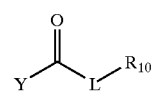

VI

In Structural Formula VI, Y and L are as defined in Structural Formula III, and $R_{10}$ is a substituted or unsubstituted alkenyl group or a group having at least one α,β-unsaturated carbonyl. The immobilized unsaturated aliphatic groups are then contacted with a polymerization solution containing a free radical initiator, a disulfide bisacrylamide and optionally containing an acrylamide to form a solid support having immobilized latent thiol groups in an acrylamide gel. The latent thiol groups can be activated by contacting the gel with a disulfide reducing agent.

In another embodiment, the polymeric solid support which is functionalized with an amine or hydroxyl reactive functional groups is reacted with a compound represented by Structural Formula III to form a solid support having immobilized latent thiol groups. In this embodiment, the solid support is preferably, cellulose, celite, poly(acrylic acid), polystyrene, cross-linked polystyrene, an agarose or cross-linked agarose, such as Sepharose or Superose, a cross-linked dextran, such as Sephadex or Sephacryl, or a composite of cross-linked agarose and dextran, such as Superdex,. The latent thiol groups are activated by removing the thiol protecting groups. Methods for removing thiol protecting groups can be found in Greene, et al., *Protective Groups in Organic Synthesis* (1991), John Wiley & Sons, Inc., pages 277–308, the teachings of which are incorporated herein by reference in their entirety.

In another embodiment, the solid support is silica, alumina, quartz or glass, and the solid support is derivatized with a latent thiol group by contacting the solid support with a compound which has a silane group or a carboxylic acid group and a latent thiol group. In a preferred embodiment, the compound can be represented by Structural Formula VII:

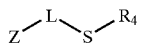

VII

In Structural Formula VII, $R_4$ and L are defined as above, and Z is a carboxylic acid group or a silane group of the formula:

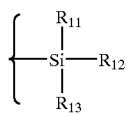

wherein $R_{11}$, $R_{12}$ and $R_{13}$ are each, independently, a halogen, a substituted or unsubstituted alkyl group, a substituted or unsubstituted aromatic group or a substituted or aralkyl group, provided that at least one of $R_{11}$, $R_{12}$ or $R_{13}$ is a halogen. "{" represents the attachment of the silane group to the linking group represented by "L".

In another embodiment, the solid support is platinum or palladium, and the solid support is derivatized with a latent thiol group by contacting the solid support with a compound that has a nitrile or an isonitrile group and a latent thiol group. In a preferred embodiment, the compound can be represented by Structural Formula VIII:

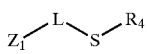

VIII

In Structural Formula VIII, $R_4$ and L are defined as above, and $Z_1$ is a nitrile or an isonitrile group.

In another embodiment, the solid support is copper and the solid support is derivatized with a latent thiol group by contacting the solid support with a compound that has a hydroxamic acid group and a latent thiol group.

The nucleic acids can be immobilized on the surface of the support in any pattern or arrangement, e.g., blocks, lines, grids or whorls. Nucleic acids with identical nucleotide sequences can be immobilized on the solid support, nucleic acids with non-identical or different nucleotide sequences can be immobilized on the solid support, and combinations of nucleic acids which contain some portion with identical nucleotide sequences and some portions which contain non-identical sequences can be immobilized on the surface of the solid support.

In particular embodiments, a plurality of nucleic acids, portions of which contain identical nucleotide sequences and portions of which contain non-identical nucleotide sequences, are attached to the solid support in a manner such that nucleic acids with non-identical nucleotide sequences are found on spatially distinct regions of the surface. The phrase "spatially distinct region" is intended to include a region on the surface of a solid support around which an imaginary perimeter can be drawn which does not overlap with the perimeter of any other region.

The term "array" is intended to include a solid support containing nucleic acids immobilized on at least one spatially distinct region of its surface. An array can contain any number of nucleic acids immobilized within any number of spacially distinct regions. The spacing and orientation of the nucleic acids can be regular, e.g., in a rectangular or hexagonal grid, or the pattern can be irregular or random. In a particular embodiment, nucleic acids containing non-identical nucleotide sequences are arranged in a regular pattern on the surface of a solid support. Such an embodiment is particularly useful, for example, in determining whether a particular set of components are present in a sample. Nucleic acids capable of detecting the presence of each component of the set can be placed in a spacially distinct region, so that in a single analysis, a determination can be made as to whether one or more of the components of the set are contained within the sample. The term "microarray" is intended to include an array in which the spacially distinct regions containing nucleic acids are relatively small.

An affinity ligand having a thiol reactive group may be contacted with a solid support having free thiols either by immersing the solid support in a solution of ligand, or by contacting a drop of ligand to the support. In the latter case, the ligand may be deposited by mechanical contact, as with a metal pin, or the ligand may be sprayed, as with a piezoelectric dispenser. When the ligand is deposited onto the surface with a pin or piezoelectric dispenser, the volume of solution containing the ligand will vary, depending on the conditions used. For example, with the Affymetrix Model 417 pin-loop spotter, the volume deposited depends on the diameter of the loop (see S. Rose, "Applications of a Novel Microarraying System in Genomics Research and Drug Discovery, *Journal of Association for Laboratory Automation*, 3:(3) 1998) and is in the range of nanoliters (nL) to picoliters (pL).

The term "sample" or "test sample" are intended to include component mixtures which can contain the target molecule. The test sample can be used directly as obtained from the source or following pretreatment. The test sample can be derived from any biological source, such as a physiological fluid, including, blood, saliva, ocular lens fluid, cerebral spinal fluid, sweat, urine, peritoneal fluid, amniotic fluid and the like, and fermentation broths, cell cultures, and chemical reaction mixtures and the like. The test sample can be pretreated prior to use, such as preparing plasma from blood, diluting viscous fluids, and the like. Methods of treatment can involve filtration, distillation, extraction, concentration, inactivation of interfering components, and the addition of reagents. In addition, a solid material such as cells which can contain the target molecule can be used as the test sample. In some instances, it may be beneficial to modify a solid test sample to form a liquid medium or to release a target molecule.

The solid supports formed by the methods of the invention can be utilized in a variety of assays. Typically, such assays include a hybridization reaction between the immobilized nucleic acid and a target molecule introduced to the solid support, e.g., contained in a test sample. It is clear to one of skill in the art that such methods can be carried out under a range of hybridization conditions utilizing wash conditions with low to high stringencies. Conditions can be selected based on the amount of similarity or differences between the nucleic acids.

"Stringency conditions" for hybridization is a term of art which refers to the conditions of temperature and buffer concentration (ionic strength) which permit hybridization of a particular nucleic acid to a second nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated by reference. The exact conditions which determine the stringency of hybridization depend not only on ionic strength, temperature and the concentration of denaturants such as formamide or urea, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined. Binding conditions for triplexes and tetraplexes can be estimated in a similar manner. A general description of stringency for hybridization and wash conditions is provided by Ausubel, F. M. et al., *Current Protocols in Molecular Biology*, Greene Publishing Assoc. and Wiley-Interscience 1987, & Supp. 49, 2000, the teachings of which are incorporated herein by reference. Factors such as probe length, base composition, percent mismatch between the hybridizing sequences, temperature and ionic strength influence the stability of nucleic acid hybrids. Thus, stringency conditions sufficient to allow hybridization of nucleic acids, can vary significantly. Such conditions can readily be determined by one of ordinary skill in the art.

Such hybridization reactions take place between nucleotide sequences which are substantially complementary. The phrase "substantially complementary" is intended to include nucleic acid sequences which are sufficiently complementary to hybridize with each other under specified conditions. Typically, complementary nucleic acids contain at least one complementary subsequence. The term "subsequence" is intended to include any contiguous segment of a larger sequence. Thus, a complementary subsequence includes at least one contiguous segment complementary to the nucleotide sequence of another nucleic acid.

Target molecules separated or detected in the assays of the invention can be amplified. The term "amplified" is intended to include primer dependent nucleic acid synthesis catalyzed by a nucleic acid polymerase. For example, the polymerase chain reaction or hereinafter "PCR" can be utilized to amplify a target molecule. The method can be used in an assay for detecting a contaminant in a sample, for medical diagnosis of a medical condition, for genetic and physical mapping of genomes, for monitoring gene expression and for DNA sequencing.

The solid supports formed by the methods of the invention can be provided in the form of kits. Such kits can contain various components. In one embodiment, a kit can contain a solid support containing a plurality of latent thiol groups. Such a kit can be provided with instructions teaching the purchaser methods for activating the latent thiol groups and for forming a covalent bond between the activated thiol groups and nucleic acids containing an appropriate acrylamide functional group. Such nucleic acids can be synthesized by the purchaser or, alternatively, they can be purchased separately from the kit of the invention. Kits containing components in addition to a solid support containing immobilized thiol groups are also within the scope of the invention. Such kits can contain components for activating the thiol groups, e.g, reducing agents and/or a wash buffer. Such kits can also contain nucleic acids with acrylamide functional groups. The nucleic acids can be identical, non-identical or a combination can be provided. Typically, components of the kits are contained in separate containers.

In an alternate embodiment, a kit can contain a solid support containing a plurality of latent thiol groups and nucleic acids containing an appropriate acrylamide functional group. Kits containing components in addition to a solid support containing immobilized thiol groups and nucleic acids containing an appropriate acrylamide functional group are also within the scope of the invention. Such kits can contain components for activating the thiol groups, e.g, reducing agents and/or a wash buffer. Typically, components of the kits are contained in separate containers.

The features and other details of the invention will now be more particularly described and pointed out in the examples. It will be understood that the particular embodiments of the invention are shown by way of illustration and not as limitations of the invention. The principle features of this invention can be employed in various embodiments without departing from the scope of the invention.

EXAMPLES

Example 1

Derivatization Of Polystyrene Microspheres With An Acrylamide-Functional Nucleic Acid FIG. 1 depicts schematically one method for covalently bonding acrylamide functional nucleic acids to a polystyrene support. In Step 1, the formation of latent thiol groups on amino-functional polystyrene is illustrated. Approximately 10 $\mu$L of amino-functional polystyrene microspheres (10% suspension) were dispersed in 80 $\mu$l of phosphate buffer (50 mM, pH=7.5). The amino-functional polystyrene microspheres had a diameter of approximately 1 $\mu$m and an amino group density of approximately 75 $\mu$eq/g (Bang's Laboratories Inc., Fisher, Ind.). To the polystyrene microsphere suspension, 368 $\mu$g of N-succinimidyl S-acetylthioipropionate (hereinafter "SATP"), (Pierce, Rockford, Ill.) in 10 $\mu$l of dimethyl sulfoxide (hereinafter "DMSO") was slowly added. This mixture was gently shaken for approximately two (2) hours at ambient temperature. The microspheres were then washed three (3) times, each time with 100 $\mu$l of phosphate buffer (50 mM, pH=7.5), by adding the phosphate buffer and mixing, centrifuging, and decanting the supernatant, to provide latent thiol microspheres after the final decanting step.

(The latent thiol derivatized microspheres, also referred to as thiolated microspheres, can optionally be dried and stored at this point for future use. If dried, the thiolated microspheres can be rehydrated in phosphate buffer prior to continuing with Step 2.) The following steps were performed to provide oligonucleotide functional polystyrene microspheres.

As illustrated, in Step 2, the activation of latent thiol (deacetylation) was described. Deacetylation buffer was prepared containing 50 mM phosphate buffer, 25 $\mu$M EDTA and 0.5 M of hydroxylamine HCl. It had a final pH of 7.5. Next, 100 μl of the deacetylation buffer was added to the latent thiol microspheres in the centrifuge tube from Step 1. The centrifuge tube was gently shaken for two (2) hours at ambient temperature. After centrifugation, the supernatant and microspheres were separated by decantation providing activated microspheres in the tube.

Step 3 describes oligonucleotide attachment. To the centrifuge tube from step 2, 100 μl of 1×TE buffer were added, along with 1.0 μl of acrylamide-modified oligonuleotide primer pair solution having a concentration of 100 μM for each oligonucleotide (Operon Technologies, Alameda, Calif.). The microsphere suspension was then gently shaken for one (1) hour at ambient temperature. Oligonucleotides covalently bound through a thioether linkage to activated microspheres (oliogonucleotide bound microspheres) were obtained.

In Step 4, an optional step of blocking the excess reactive thiol groups is described. Excess thiol groups on the oligonucleotide bound microspheres can be blocked, if desired. To block the excess thiol groups on the microspheres, 277 μg of iodoacetamide (Aldrich Chemical Co., Milwaukee, Wis.) dissolved in 10 μl of 1×10 mM Tris-HCL pH 8.3; 1 mM EDTA buffer (hereinafter "TE buffer") was added to the oligonucleotide bound microspheres of Step 3. The centrifuge tube and its contents were then shaken for one (1) hour at ambient temperature. The TE buffer was decanted off the microspheres. Then, the microspheres were washed three (3) times with 100 μl each of TE buffer to provide capped, oligonucleotide bound microspheres. After decanting the last wash, the capped oligonucleotide bound microspheres in the tube were ready for use in a PCR reaction, for example, as illustrated in U.S. Pat. No. 4,683,202, the disclosure of which is incorporated herein by reference. (Alternatively, the capped oligonucleotide microspheres can be dried and stored at this point for future use. If dried, the capped oligonucleotide microspheres can be rehydrated in phosphate buffer prior to use.)

Exampel 2

Array Formation On An Aminoalkyl Glass Slide

A glass slide having a plurality of amine groups attached in a substantially uniform spatial pattern to a flat surface thereof (Part #S 4651, aminoalkyl silane coated slides, Sigma Chemical Co., St. Louis, Mo., 1999 catalog) was submerged for two (2) hours at ambient temperature in a solution of 15 mM SATP in 50 mM phosphate buffer pH 7.5, 10% DMSO. The glass slide was then washed three (3) times with 50 mM, pH 7.5 phosphate buffer by submerging the glass slide in phosphate buffer. A glass slide having a plurality of latent thiolated groups was formed.

The glass slide was submerged in a solution of deacetylation buffer which contains 50 mM of phosphate buffer pH 7.5, 25 FM of EDTA and 0.5 M of hydroxylamine-HCl, for two (2) hours at ambient temperature to provide a glass slide having a plurality of activated thiol groups.

A plurality of acrylamide-modified oligonucleotides were attached to the activated thiol groups. A glass slide was uniformly modified with acrylamide-modified nucleic acids by submerging the activated glass slide in a 100 μM solution of acrylamide-modified oligonucleotide in 1×TE buffer (Acrydite™ acrylamide-modified oligonucleotide obtained from Operon Technologies, Alameda, Calif.) for one (1) hour at ambient temperature.

A plurality of acrylamide-modified oligonucleotides, each having a different sequence, were deposited onto the slide in spatially distinct regions. Deposition of the oligonucleotides onto the activated array was performed manually, although it could also have been performed automatically (e.g., using a pipetting robot). Using a micropipette dipped into an acrylamide-modified oligonucleotide solution, an aliquot of the solution was transferred to a predetermined region on a glass slide having activated thiol groups. A second acrylamide-modified oligonucleotide was then deposited onto a second region that is spatially distinct from the first region, using the same procedure with a fresh micropipette.

Alternatively, a capillary dispenser, for example, one as illustrated in U.S. Pat. No. 5,807,522, the teachings of which are incorporated herein by reference, can be used. Other spotting methods known to those skilled in the art, which permit the regions of the array to be arranged so that the oligonucleotide sequences are appropriately spaced, can also be used.

In an alternative embodiment, random arrays are formed using an ink-jet spray apparatus such as, for example, the apparatus illustrated in U.S. Pat. No. 5,599,695, the teachings of which are incorporated by reference in their entirety. In yet another embodiment, regions of an array can be defined utilizing a mask, such as those utilized in photolithography.

After deposition of all oligonucleotides on the array, activated thiol groups that have not been covalently linked to an acrylamide-modified oligonucleotides are blocked. For example, the method of Step 4 in Example 1 above can be used to inactivate remaining thiol groups. Other chemical treatments known to those of skill in the art can also be utilized.

Example 3

Array Formation on a Polystyrene Support

A polystyrene flat support having a plurality of amine groups attached in a substantially uniform spatial pattern to a flat surface thereof is submerged for two (2) hours at ambient temperature in a solution of 15 mM SATP in dimethyl sulfoxide-phosphate buffer. Then, the polystyrene flat support is washed three (3) times with 50 mM, pH=7.5 phosphate buffer, submerging the polystyrene flat support in phosphate buffer to provide a polystyrene flat support having a plurality of latent thiolated sites.

Deacetylation buffer which contains 25 μM EDTA, 0.5 M hydroxylamine-HCl in 50 mM phosphate buffer is prepared with a final pH of 7.5. It is mixed with 100 mM acrylamide-modified oligonucleotides (Operon Technologies, Alameda, Calif.) in 1×TE buffer. The solution is selectively spotted onto the latent thiol sites in predefined regions. Since only selected areas on the support are provided with activated thiol groups through contact with the deacetylation buffer, only those regions are available for binding acrylamide-modified oligonucleotides. Thus, latent regions remain and can be used to separate the regions to which oligonucleode has been covalently bound.

Example 4

Array Formation With Predefined Patterns

In yet another alternative embodiment, a glass slide can be provided with amine groups in a predefined pattern. The amine groups can then be converted to latent thiol groups and the support treated as described in Example 2.

Example 5

Array Formation on an Acrylate Slide

Figure 2A:
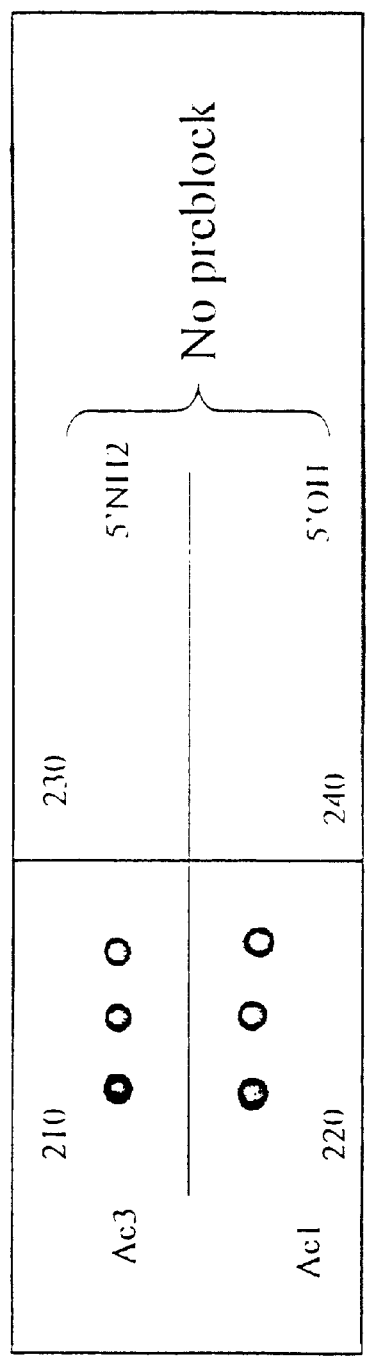
FIG. 2A is a representation of a solid support selectively treated to activate latent thiol groups.
Figure 2B:
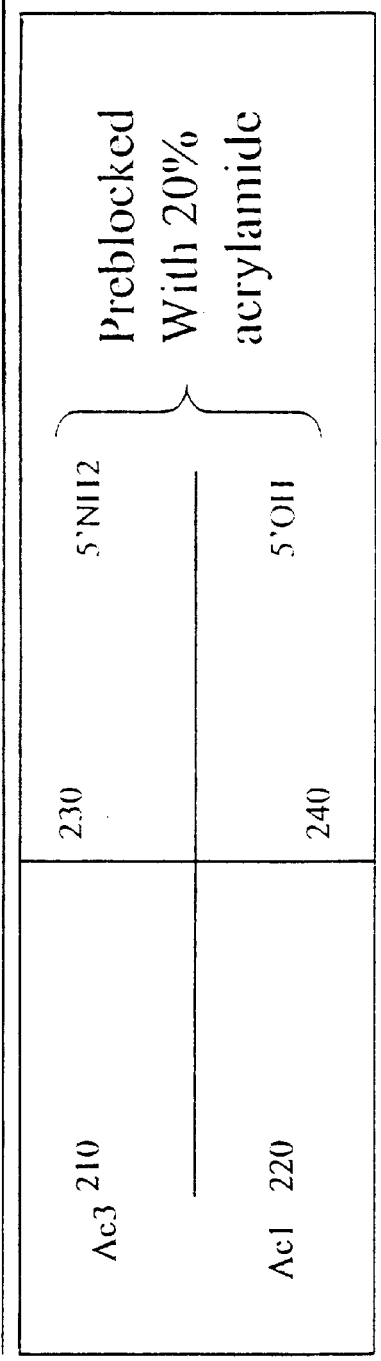
FIG. 2B is a representation of a solid support in which reactive groups are locked, then exposed to acrylamide functional oligonucleotides.

This example demonstrates attachment of acrylamide-modified oligonucleotide probes to a crosslinked polyacrylamide gel support containing the disulfide bisacrylamide crosslinker N,N'-bis(acryloyl)cystamine, (hereinafter "BAC", Fluka, Buchs, Switzerland). Acrylamide groups on the oligonucleotide probes were added during synthesis using commercially available acrylamide phosphoramidites (Acrydite™ phosphoramidites I and II, Mosaic Technologies, Waltham, Mass.). Solid phase hybridization performance of 5'-methacrylamide-modified oligonucleotide probes, indicated by "Ac1" (generated with Acrydite™ I) 220 were compared with 5'-acrylamide-modified oligonucleotide probes, indicated by "Ac3" (generated with Acrydite™ III) 210. In all cases, (FIGS. 2A, 2B), oligonucleotide probes were spotted onto thiol containing gel-coated slides and allowed to react. The slides were washed to remove unbound probe, and then hybridized to a fluorescently labeled oligonucleotide target to reveal the hybridization performance of the immobilized probes. Control experiments (not shown) demonstrated that when tris(2-carboxyethyl) phosphine hydrochloride (hereinafter "TCEP") treatment was omitted, images similar to FIG. 2B were produced, thus, demonstrating that activated, reduced thiols (but not latent thiols) were required for probe binding. FIG. 2B shows that 5'-acrylamide probe binding was prevented by pretreating the TCEP-treated slide with excess monomer acrylamide, suggesting that the acrylamide function of the probes are important for binding. FIG. 2A also demonstrates that 5' amino 230 and 5'hydroxyl 240 modified oligonucleotide probes show low binding to gels containing activated thiol groups.

Step 1: Preparation of Acrylate Slide Bound to Acrylamide Gel Layer

Aqueous acrylamide solution was prepared using 6% acrylamide (29:1 ratio of acrylamide monomer to bisacrylamide (BioRad laboratories, Inc.; Hercules, Calif.) and 0.5% (wt/v) N,N'-bis(acryloyl)cystamine (Fluka, Buchs, Switzerland)) in 100 mM sodium borate buffer pH 9 (hereinafter "SBB"). The aqueous solution was cooled on ice. A 100 µl aliquot was mixed with 1 µl fresh 10% ammonium persulfate (hereinafter "APS", BioRad Laboratories, Inc., Hercules, Calif.) and 1 µl N,N,N',N'-tetramethylethylenediamine (hereinafter "TEMED"; BioRad, Hercules, Calif.) diluted 10:1 with water to provide an acrylamide gel solution. Next, 30 µl of the acrylamide gel solution were pipetted onto an acrylate slide (Cat# ACR-25C, CEL Associates, Inc., Houston, Tex.) that is at room temperature. The acrylamide gel solution was overlaid with a glass coverslip (24×50 mm) taking care not to create any air bubbles or gaps. The acrylamide gel solution was allowed to polymerize on the acrylate slide for at least 45 minutes at room temperature. The coverslip was removed leaving an acrylamide gel layer having latent thiol groups bound to the acrylate slide.

(At this point, the slides can be also be dried and stored for later use after rehydration.)

Step 2: Activation of the Latent Thio Groups

The acrylate slides each having a thio-derivatized acrylamide gel layer were placed in 20 mM TCEP (Fluka; Buchs, Switzerland) in 100 mM SBB pH 9 and were incubated for 15 minutes.

The slides were washed two (2) times in TE buffer, then rinsed with water and allowed to air dry.

Step 3: Oligonucleotide Attachment to Acrylamide Gel

The slides were spotted within 30 minutes of TCEP treatment with oligonucleotides modified as described. Spotting solutions were prepared with 100 mM SBB pH 9 and 20 µM oligonucleotide (Operon, Alameda, Calif.) containing Acrydite m11 modification, 5'Acrydite I modification, 5' NH2 modification, or without a 5' modification. Individual spots of 0.5 µl of each solution (10 pmoles) were placed onto each slide in triplicate. The slides were placed in a nitrogen box and incubated for one (1) hour at room temperature. Then, the slides were washed two (2) times with TE+0.2M sodium chloride (hereinafter "NaCl"). The slides were washed two (2) times in TE pH8 and allowed to dry.

Step 4: Oligonucleotide Detection By Hybridization

An aliquot of 60 µl hybridization mix (10 µM complementary fluorescent oligonucleotide (OPERON, Alameda, Calif.) in 5×SSPE+0.2% SDS was placed on the slide and the slide was overlaid with a coverslip. The slides were allowed to hybridize for one (1) hour at room temperature in a humid hybridization chamber (Coming, Coming, N.Y.). After one (1) hour, the slides were washed two (2) times with 1×SSPE+0.1%, SDS. Then, each slide was washed one (1) time with TE at pH 8 and was allowed to air dry.

The slide is imaged dry in a fluorescent imager (Molecular Dynamics, Fluorimager 595, Sunnyvale, Calif.).

Example 6

Microarray Formation on an Gel-Coated Support and Comparison of Blocking Agents

Step 1: Preparation of gel-coated slide supports

A polymerization solution was prepared with 6% acrylamide (29:1), and 0.5% BAC (wt/v), in 100 mM SBB pH9. (BAC required heating and vortexing to go into solution) 1 µl fresh 10% APS (made same day) and 1 µl of 10:1 dilution of $H_2O$:TEMED were added to 100 µl of the solution and mixed thoroughly. 10 µl of solution were pipetted onto an Acrylate Slide (CEL Associates, Inc., ACR-25C) and overlaid with a glass overslip (18×18 mm), taking care not to create any air bubbles or gaps in the solution. The acrylamide layer was allowed to polymerize at least 20 minutes at room temperature. After the slides were rinsed in TE and allowed to air dry, they were ready for spotting of oligo.

Step 2: Activation of the Latent Thiol Group

Spotting solutions were prepared from 20 µM of Acrydite™ oligo and 100 mM TCEP, all in 100 mM SBB at pH 9.

35 µl of various solutions were prepared and placed in a microtiter plate.

TABLE 1

| Well # | oligo | Well Col | Well Row | Probe | Replicate | Pin # | Slide Abs | Slide Abs |
|---|---|---|---|---|---|---|---|---|
| A1 | Tryp 370 | 1 | 1 | 0 | 1 | | 5.5 | 40 |
| A3 | Tryp 355 | 3 | 1 | 0 | 1 | | 5.8 | 40 |
| A5 | Tryp 575 | 5 | 1 | 0 | 1 | | 6.1 | 40 |
| A7 | no oligo | 7 | 1 | 0 | 1 | | 6.4 | 40 |
| A9 | blank | 9 | 1 | 0 | 1 | | 6.7 | 40 |
| A11 | blank | 11 | 1 | 0 | 1 | | 7 | 40 |
| A2 | Bglobar1269 | 2 | 1 | 0 | 2 | | 14.5 | 40 |
| A4 | Bglobar1287 | 4 | 1 | 0 | 2 | | 14.8 | 40 |
| A6 | Bglobar490 | 6 | 1 | 0 | 2 | | 15.1 | 40 |
| A8 | ANF401 | 8 | 1 | 0 | 2 | | 15.4 | 40 |
| A10 | no oligo | 10 | 1 | 0 | 2 | | 15.7 | 40 |
| A12 | blank | 12 | 1 | 0 | 2 | | 16 | 40 |

Step 3: Oligonucleotide Attachment to Acrylamide Gel

The slides were arrayed on a GMS spotter as follows:

The slides were incubated on a lab bench at room temperature for one (1) hour. After one (1) hour, the slides were soaked for 30 minutes in 20% dimethylacrylamide (hereinafter "DMA") or 20% 2-hydroxyethylmethacrylate (hereinafter "HEMA") in 100 mM SBB at pH 9. The slides were washed two (2) times with TE +0.2M NaCl. Then, the slides were washed once in TE and allowed to dry.

Step 4: Oligonucleotide Detection by Hybridization

Adhesive hybridization chambers were attached to the slides and 90 III of the hybridization mixture were added to slides: eDNA prepared from 50 ng input globin RNA in 4×SSPE+0.2% Tween. The slides were hybridized overnight at 55° C. in a humid hybridization chamber. After incubation, the slides were washed two (2) times with 1×SSPE+0.1% Tween. Then, the slides were washed one (1) time with TE and allowed to air dry. The slides were imaged dry.

Figure 3A:
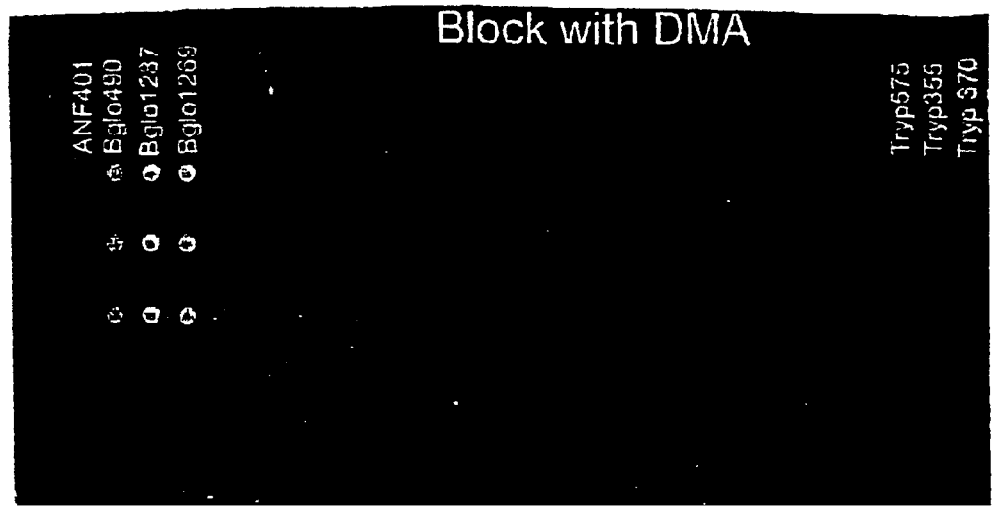
FIG. 3A is a photograph showing results of microarray formation on a N, N' bis(acryloyl)cystamine (BAC) coated slide in which excess thiol groups were blocked with dimethylacrylamide (DMA).
Figure 3B:
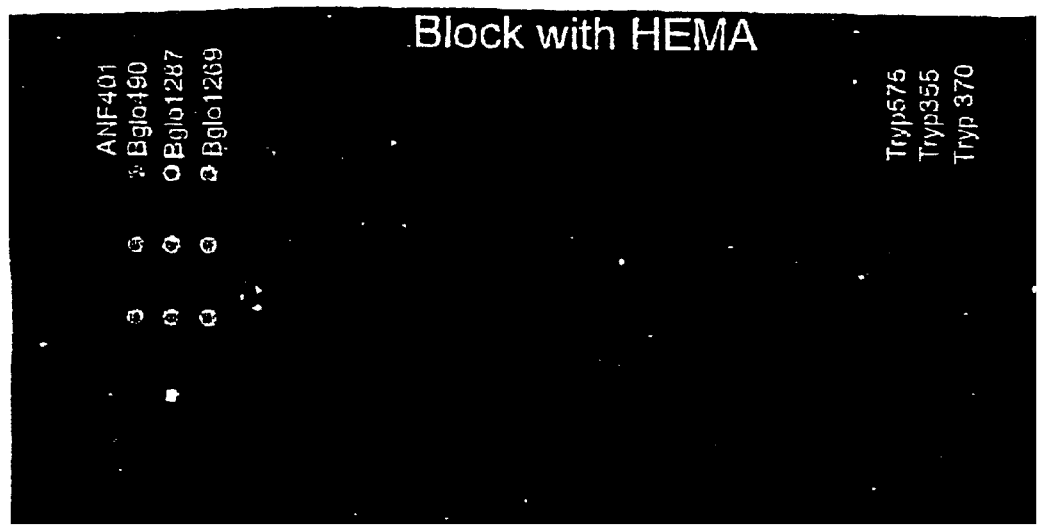
FIG. 3B is a photograph showing results of microarray formation on a N, N' bis(acryloyl)cystamine (BAC) coated slide in which excess thiol groups were blocked with 2-hydroxymethacrylate (HEMA).

When quantified, blocking with HEMA is comparable to slide with DMA. Background with HEMA block is slightly higher, but the difference is not significant. The results, both when blocked with DMA and blocked with HEMA, are shown in FIGS. 3A–3B.

Example 7

Preparation of 0.5% bis(acryloyl) cystamine (BAC) Thin Gel Supports

| The following were mixed in a 15 ml tube: | | Final conc: |
|---|---|---|
| 0.5 ml dimethylformamide (DMF) | 5.0% | |
| 50 mg N,N'-bis(acryloyl) cystamine (BAC) | 0.5% | (19.2 mM) |
| 1.5 ml 40% stock acrylamide/bis solution | 6.0% | (844 mM) |
| 2.0 ml 500 mM Tris-Glycine buffer pH 9.0 | 100 mM | |
| 6.0 ml water | 10 ml total volume | |

1 ml of the above solution was placed on ice and added to:

| 1 μl 1% SDS | 0.001% |
|---|---|
| 10 μl 10% aqueous APS | 0.1% |
| 10 μl 10% aqueous TEMED | 0.1% |

10 μl of the above solution was pippetted onto a microscope that was coated with an acrylic silane (CEL Associates, Inc., Houston, Tex.) and overlaid with a glass coverslip (18×18 mm) taking care not to create any air bubbles or gaps in the solution. The solution was allowed to polymerize for 30 minutes at room temperature. The coverslip was removed using a razor blade. The slides were washed in TE buffer and allowed to dry at room temperature.

Example 8

Preparation of 4[(1-oxo-3-[[2-[(1-oxo-2-propenyl)-amino]ethyl]dithio]propyl]amino butanoic acid (AEMA) Thin Gel Supports 123 mg of AEMA were dissolved in 0.5 ml dimethyl formamide (hereinafter "DMF") and 1.5 ml water. After the AEMA was dissolved the following was added:

| | Final conc: |
|---|---|
| 1.5 ml 40% stock acrylamide/bis solution | 6.0% (844 mM) |
| 2.0 ml 500 mM Tris-Glycine buffer pH 9.0 | 100 mM |
| 5.0 ml water | 10 ml total |

1 ml of the above solution was taken, placed on ice and the following was added:

| 1 μl 1% SDS | 0.001% |
|---|---|
| 10 μl 10% aqueous APS | 0.1% |
| 10 μl 10% aqueous TEMED | 0.1% |

10 μl of the above solution was pippetted onto a microscope that was coated with an acrylic silane (CEL Associates, Inc. Houston, Tex.) and overlaid with a glass coverslip (18×18 mm) taking care not to create any air bubbles or gaps in the solution. The solution was allowed to polymerize for 30 minutes at room temperature. The coverslip was taken off using a razor blade. The slides were washed in TE buffer and allowed to dry at room temperature.

Example 9

Preparation Of Thin Gel Supports With reduced BAC, β-Mercaptoethanol Method

| The following was added to a 15 ml tube: | |
|---|---|
| 100 mg BAC | 1.0% (0.384 mmole) |
| 0.5 ml DMF | |
| 0.5 ml water | |

After BAC dissolved, the following was added:
  27.5 ml β-mercaptoethanol dissolved in 0.5 ml water (0.384 mmole)
The solution was allowed to react for 1–12 hours at room temperature.

| After incubation the following was added: | Final conc: |
|---|---|
| 1.5 ml 40% stock acrylamide/bis solution | 6.0% (844 mM) |
| 2.0 ml 500 mM Tris-Glycine buffer pH 9.0 | 100 mM |
| 5.0 ml water | 10 ml total |

1 ml of the above solution was taken, placee on ice and the following was added:

| 1 μl 1% SDS | 0.001% |
|---|---|
| 10 μl 10% aqueous APS | 0.1% |
| 10 μl 10% aqueous TEMED | 0.1% |

10 μl of the above solution was pippetted onto a microscope that was coated with an acrylic silane (CEL Associates, Inc. Houston, Tex.) and overlaid with a glass coverslip (18×18 mm) taking care not to create any air bubbles or gaps in the solution. The solution was allowed to polymerize for 30 minutes at room temperature. The coverslip was taken off using a razor blade. The slides were washed in TE buffer and allowed to dry at room temperature.

Example 10

Preparation Of Thin Gel Supports With Reduced BAC, Thioacetic Acid Method

| The following was added to a 15 ml tube: | |
|---|---|
| 100 mg BAC | 1.0% 0.384 mmole |
| 0.5 ml DMF | |
| 0.5 ml water | |

After the BAC was dissolved, the following was added:

| 43.8 mg thioacetic acid | 0.384 mmole |
|---|---|

After the incubation, the following was added:

| | Final conc: |
|---|---|
| 1.5 ml 40% stock acrylamide/bis solution | 6.0% (844 mM) |
| 2.0 ml 500 mM Tris-Glycine buffer pH 9.0 | 100 mM |
| 5.0 ml water | 10 ml total |

1 ml of the above solution was taken, placed on ice and the following was added:

| 1 µl 1% SDS | 0.001% |
|---|---|
| 10 µl 10% aqueous APS | 0.1% |
| 10 µl 10% aqueous TEMED | 0.1% |

10 µl of the above solution was pippetted onto a microscope that was coated with an acrylic silane (CEL Associates, Inc. Houston, Tex.) and overlaid with a glass coverslip (18×18 mm) taking care not to create any air bubbles or gaps in the solution.

The solution was allowed to polymerize for 30 min. at room temperature. Take off the coverslip using a razor blade. Wash the slides in TE buffer and allow to dry at room temperature.

Example 11

Comparison of BAC, AEMA, and reduced BAC Supports For Microarray Hybridization; Effect Of Buffer And Glycerol In Spotting Solutions Three different types of supports were prepared.

Standard support containing 0.5% BAC (19.2 mM disulfide bonds yielding 38.4 mM thiol groups after reduction). The preparation is described in Example 7 above.

AEMA support containing 38.4 mM AEMA and 38.4 mM thiol groups bound to the gel after reduction. The preparation is described in Example 8 above.

BAC+ME gel pad containing 38.4 mM BAC and 38.4 mM thiol groups bound to the gel after reduction. The preparation is described in Example 9 above.

After polymerization, two slides of each type were washed and treated with 10 mM TCEP solution in 100 mM sodium carbonate, pH 10 for 20 min. Another slide prepared with a gel layer containing no BAC was treated the same way. The slides were washed four (4) times in 1×SSPE buffer containing 0.1% SDS. Then the slides were washed two (2) times in 10 mM TE buffer pH 8.

The conversion of disulfide groups into thiol groups was confirmed by spotting 0.5 µl of 1 mM 5,5'-dithio-bis-(2-nitrobenzoic acid) (hereinafter "DTNB") solution in 100 mM phosphate buffer pH 8 on the gel. The spot turned yellow on AEMA and BAC containing gel layers, but remained colorless on a control slide with just acrylamide gel layer. This indicated that all TCEP was eluted from gel layers.

A series of solutions of 50 µl volume was prepared for spotting on slides. The solutions contained different concentrations (3, 10 and 30 mM) of Acrydite™-modified DNA oligonucleotide BD 1216 (complementary probe for rabbit globin cDNA target) in either 100 mM Tris-Glycine pH 9 or 100 mM sodium carbonate pH 10 buffer. Also, solutions containing 10 mM oligo and 10% or 20% glycerol were prepared. (Glycerol containing solutions are less sensitive to humidity of air during spotting and give higher yields of DNA probes binding in low and moderate humidity) In this experiment, all gel solutions were reduced with TCEP before spotting and no TCEP was added into spotting solutions.

The solutions were placed in a microplate well (Microseal 96 V-bottom microplates, MJ Research, MA) and the arrays were spotted using a Genetic Microsystems 417 Arrayer (Affymetrix, Santa Clara, Calif.) and incubated overnight at room temperature.

The residual activated thiols were quenched by soaking the slides in 10% acrylamide solution, 100 mM sodium carbonate buffer pH 10, for 20 minutes. to improve background between spots, then washed two (2) times in 10 mM TE+200 mM NaCl, followed by two (2) times in 10 mM TE and dried.

Hybridization was carried out overnight at 55° C. in plastic chambers with rabbit globin CDNA labeled with Cy3 fluorescent dye. Concentration of cDNA was 50 ng/ml of hybridization buffer (4×SSPE containing 0.02% Tween 20). After hybridization, the slides were washed three (3) times in 1×SSPE buffer and briefly washed two (2) times in 10 mM TE buffer, then dried using nitrogen.

The arrays were scanned with ScanArray 4000 scanner (GSI Lumonics, Watertown, Mass.) using green line 543.5 nm of HeNe laser for excitation. The laser power was set at 90% and photomultiplier power (PMT) was set at 60%. The data was analyzed using ImageQuant 5.1 software (Molecular Dynamics, Sunnyvale, Calif.). The background signal from an unspotted position on the microarray was subtracted from the total fluorescence signal of each hybridized probe spot.

Figure 6:
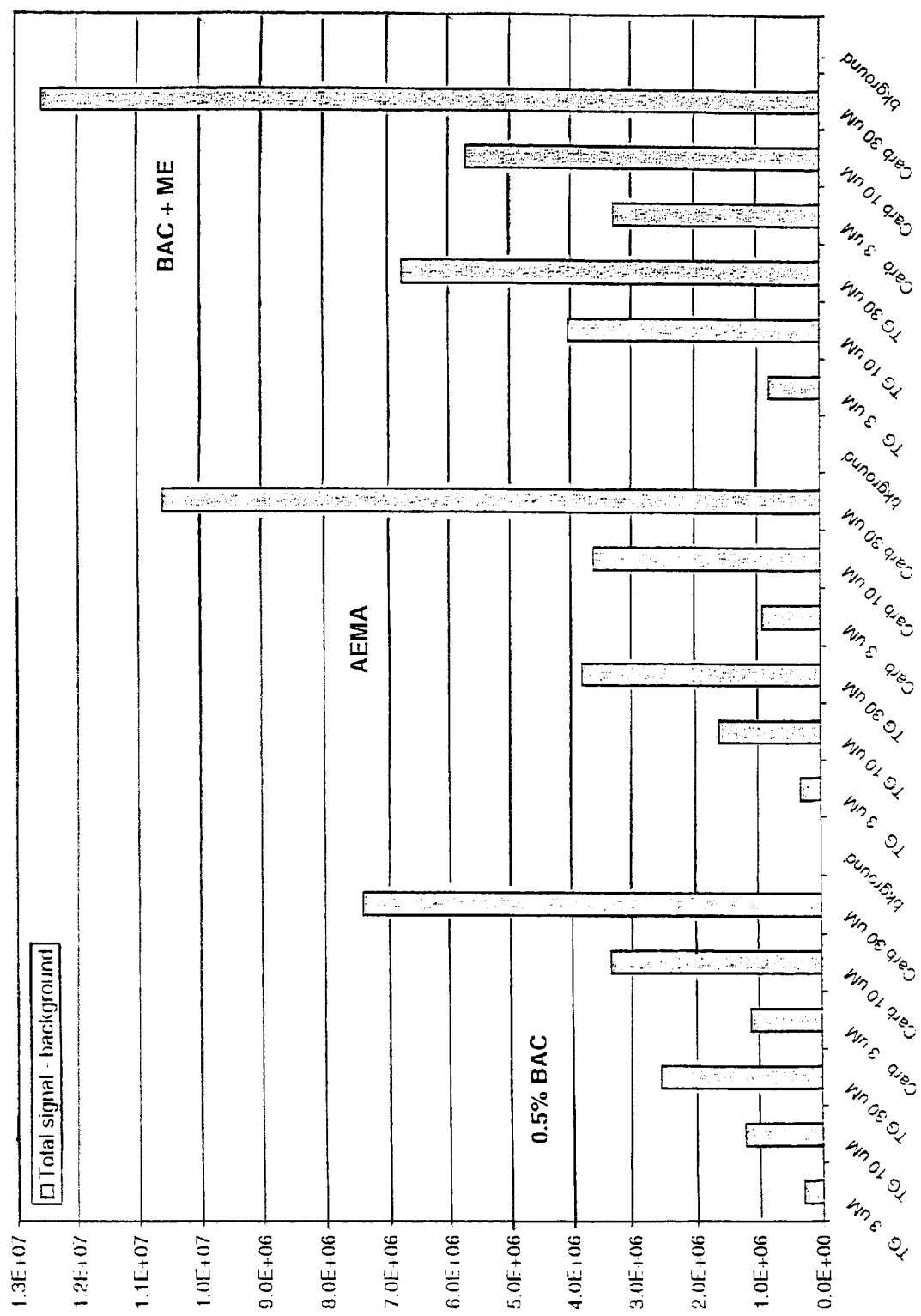
FIG. 6 is a bar graph illustrating the results obtained from a comparison of hybridizations performed using Tris-Glycine buffer and those performed using carbonate buffer.
Figure 7:
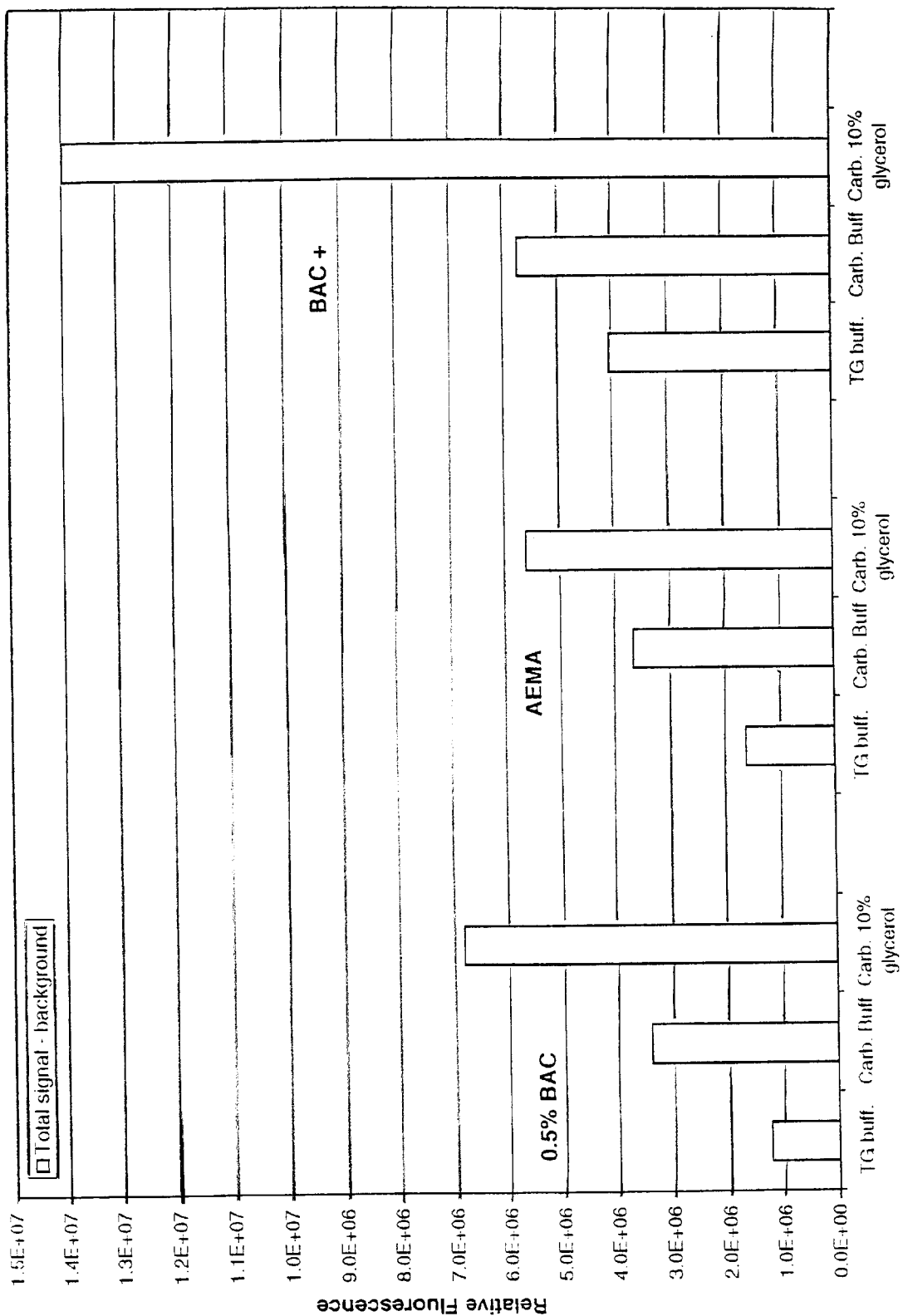
FIG. 7 is a bar graph illustrating the results of an experiment showing the influence of buffer and glycerol in spotting solution on hybridization signal for 10 $\mu$l probe spots.

The corrected fluorescence intensity data are plotted in FIGS. 6 and 7. FIG. 7 compares the Tris-Glycine buffer with the carbonate buffer. At each concentration of probe oligonucleotide tested, better hybridization signals were obtained when the probes were spotted with the carbonate buffer system. FIG. 7 shows data only for the 10 µM probe spots.

In addition, slightly better signals were obtained using the monofunctional disulfide acrylamnide, AEMA. Similar enhancement of hybridization signals resulted from using a gel layer containing BAC that had been reduced with an equimolar amount of mercaptoethanol prior to gel polymerization. Similar hybridization enhancements were also obtained from gel layers containing BAC that had been reduced with thioacetic acid prior to gel formation, as described in Example 10 (data not shown). While not wishing to be bound by theory, the enhancement may result from the fact that BAC derived thiols in gels cast with unreduced BAC, as in the BAC protocol of Example 7, may be held in close proximity after reduction in the gel, and therefore may reform the disulfide, thereby reducing the number of thiol groups available for probe binding.

Example 12

Preparation of Acrylate Slides with 1–6% BAC Polymerization In Organic Solvent Without Comonomer Acrylate slides were co-polymerized in BAC solutions containing concentrations of BAC ranging from 1% to 6%. A 1% BAC coated slide was made by mixing 3 ml of 10% BAC in DMF; 12 ml of DMF; 15 ml of water and 600 µL of 25% APS; 100 µL TEMED. After mixing, this solution was dispensed into a container with four acrylate slides; the solution was allowed to polymerize overnight at room temperature. A white homogeneous gel-like material signaled the visible onset of polymerization. The BAC acrylate slides were then removed from the solution and rinsed in deionized water with gentle rubbing to remove the visible white film formed on the BAC acrylate slide.

After treatment with TCEP to generate active thiols, the slides were spotted with an Acrydite™ oligonucleotide (50 mer) designed to hybridize to cDNA transcribed from the MRNA of the rabbit beta-globin gene. The concentrations of 50-mer used for the spots were 30 µM, 10 µM, 5 µM, 1 µM, and 0 µM. Acrydite™ modified oligonucleotide bound to the BAC acrylate slide was hybridized overnight at 55° C. in 4×SSPE; 0.02% Tween20® to Cy3-dUTP labeled cDNA (prepared from rabbit reticulocyte polyA+mRNA (Gibco-BRL; Life Technologies; Rockville, Md.) with an arrayTRACKER™ Standard Labeling cDNA Kit (Cat. #490–100, Displays Systems Biotech, Inc.; Vista, Calif.) in accordance with the instructions provided with the kit using the following modification: After the final precipitation in the display systems protocol, the cDNA preparation was resuspended in 40 µL buffer (4×SSPE; 0.02% Tween20®), and this mixture was run through a G25 spin column (Cat. # 27-5325-01 Amersham Pharmacia, Microspin G-25 column). The hybridized spotted slide was washed three (3) times in 1×SSPE buffer containing 0.02% Tween20®, then in TE, and then dried with a stream of nitrogen. The hybridized oligonucleotide spotted slide was imaged with a GSI Lumonics ScanArray 4000 Microarray Analysis System (GSI Lumonics, Inc.; Billerica, Mass.).

The results demonstrated that the amount of cDNA bound depends on the amount of BAC used to prepare the slide. Optimal signals are seen with BAC concentrations of 1–3%

TABLE 2

Effect of BAC conc

| slide | % BAC | Signal | Background |
|-------|-------|--------|------------|
| 01 | 1 | 3,839 | 71 |
| 05 | 0.5 | 1,798 | 52 |
| 06 | 1.5 | 4,275 | 67 |
| 07 | 3 | 7,479 | 75 |
| 08 | 6 | 3,815 | 83 |

Signal—sum of the RFUs (in thousands) for each pixel in an area corresponding to the region of the spotted oligo
Back—sum of the RFUs (in thousands) for each pixel in an area of equal size, where no oligo was spotted.

Example 13

Preparation of Acrylate Slides with BAC-Comonomer-Polymerization in Organic Solvent A procedure similar to that in Example 7 was used to make slides with 2% BAC, with various amounts of P400mm. To make a slide with a coating of 2%/BAC-1% P400mm, four acrylate slides were immersed in a solution made by mixing: 3.6 ml of 10% BAC in DMF; 5.4 ml of DMF; 9 ml of water; 180 µL of P400mm; 240 µL of 25% APS; 40 µL TEMED. After standing at room temperature, the appearance of the solution was noted. The BAC acrylate slides were then removed from the solution and rinsed in deionized water. In cases where a film was visible on the slides, gentle rubbing was used to remove the visible white film. The BAC acrylate slides were again washed in water, and then dried with a stream of nitrogen.

After treatment with TCEP to generate active thiols, the slides were spotted with an Acrydite™ modified oligonucleotide (50 mer) designed to hybridize to cDNA transcribed from the mRNA of the rabbit beta-globin gene. The concentrations of 50-mer used for the spots were 30 µM, 10 µM, 5 µM, 1 µM, and 0 µM. Acrydite™ modified oligonucleotide bound to the BAC acrylate slide was hybridized overnight at 55° C. in 4×SSPE; 0.02% Tween20® to Cy3-dUTP labeled cDNA (prepared from rabbit reticulocyte polyA+MRNA (Gibco-BRL; Life Technologies, Rockville, Md.) with an arrayTRACKER™ Standard Labeling cDNA Kit, (Cat. #490-100, Displays Systems Biotech, Inc.; Vista, Calif.) in accordance with the instructions provided with the kit, except that after the final precipitation in the display systems protocol, the cDNA preparation was resuspended in 40 µL of buffer (4×SSPE; 0.02% Tween20®), and this mixture was run through a G25 spin column (Cat. #27-5325-01, Amersham Pharmacia, Microspin G-25 column). The hybridized spotted slide was washed three (3) times in 1×SSPE buffer containing 0.02% Tween20®, then in TE, and then dried with a stream of nitrogen. The hybridized oligonucleotide spotted slide was imaged with a GSI Lumonics ScanArrayR 4000 Microarray Analysis System (GSI Lumonics, Inc.; Billerica, Mass.).

Addition of P400mm in the range of 0.5 to 4% (v/v) was seen to change the nature of the precipitate formed during polymerization reaction. Depending on the concentration of P400mm, the solution formed a clear gel, a cloudy gel, or no visible gel i.e., remained a liquid. When the solution remained a liquid, no film was formed on the slides, and the rubbing step above was not necessary.

The following Table shows the results obtained for slides prepared with different concentrations of P400mm in 2% BAC.

TABLE 3

| Slide # | % P400 mm | Signal* Rfu | Background* Rfu | Film Appearance After Polymerization |
|---------|-----------|-------------|-----------------|--------------------------------------|
| 01 | 0.0 | 796 | 97 | White, soft gel |
| 02 | 0.5 | 3,188 | 26 | White, soft gel |
| 03 | 1.0 | 4,243 | 68 | Bluish, grey firm gel |
| 04 | 2.0 | 2,530 | 45 | Clear, liquid |
| 05 | 4.0 | 637 | 34 | Clear, firm gel |

*Signal is the sum of the RFUs (in thousands) for each pixel in an area corresponding to the region of the spotted oligonucleotide.
*Background is the sum of the RFUs (in thousands) for each pixel in an area of each size, where no oligonucleotide was spotted.

The data also showed that the amount of cDNA bound was dependent on both the amount of comonomer, and the concentration of 50-mer oligo used in spotting, as shown in the following table:

TABLE 4

Effect of Conc of spotted oligo

| slide | oligo | % BAC | % p400 mm | signal | S-B | S/B |
|---|---|---|---|---|---|---|
| 01 | 30 | 2 | 0 | 796 | 699 | 8.2 |
|  | 10 | 2 | 0 | 307 | 210 | 3.2 |
|  | 5 | 2 | 0 | 245 | 148 | 2.5 |
|  | 1 | 2 | 0 | 150 | 53 | 1.5 |
|  | 0 | 2 | 0 | 97 | 0 | 1.0 |
| 03 | 30 | 2 | 1 | 4,243 | 4,175 | 62 |
|  | 10 | 2 | 1 | 2,200 | 2,132 | 32 |
|  | 5 | 2 | 1 | 1,308 | 1,240 | 19 |
|  | 1 | 2 | 1 | 406 | 338 | 5.9 |
|  | 0 | 2 | 1 | 68 | 0 | 1.0 |

Oligo—concentration (micromolar) of oligo spotted onto thiol slide.
Slide 01 was prepared with 2% BAC
Slide 05 was prepared with 2% BAC/1% p400mm
Signal—sum of the RFUs for each pixel in an area corresponding to the region of the spotted oligo
S-B signal minus the signal for spot with 0 oligo.
S/N signal divided by the signal for spot with 0 oligos.

Figure 4:
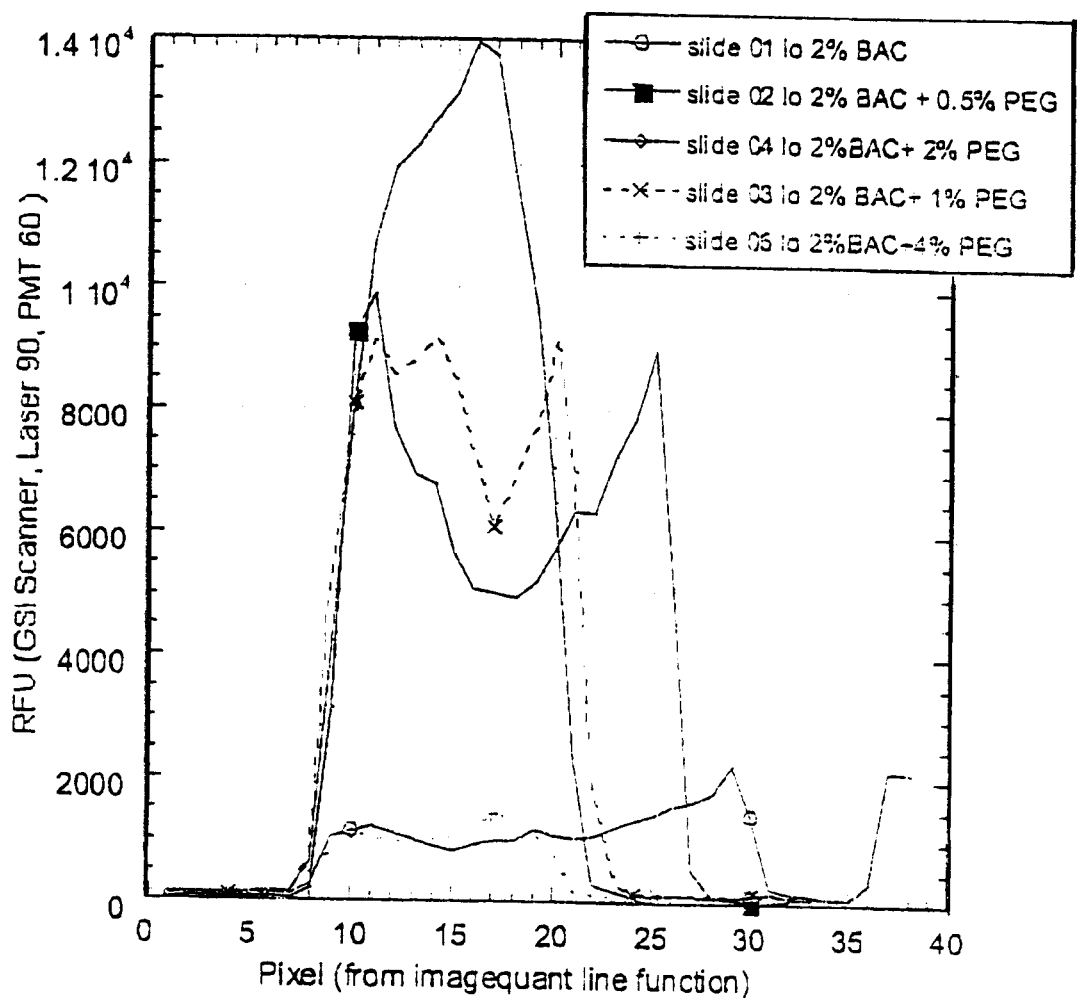
FIG. 4 is a plot of fluorescent intensity across a spot for slides prepared with 2% N, N' bis(acryloyl)cystamine (BAC) or 2% N, N' bis(acryloyl)cystamine(BAC) plus P400 mm.

Addition of comonomer also results in a change in the size of the spot made by the oligonucletide in solution. FIG. 4 shows a plot of fluorescent intensity across a spot for slides prepared with 2% BAC or 2% BAC plus P400mm at the different concentrations.

Example 14

Preparation of Acrylate Slides with BAC-Polymerization in Water

1% BAC in water coated slides were prepared as follows: 0.5 g of BAC was dissolved in 50 ml of deionized water at 70° C. Acrylate slides were completely submerged in the heated BAC solution. 1.0 ml of 0.05% APS and 1.0 ml of 0.05% TEMED were added. The container was sealed and shaken for 1 minute. The polymerization reaction was complete within several minutes. A white precipitate of polyBAC formed. After removal of the macroscopic polyBAC particulate with water, the acrylate slides appeared coated with a homogeneous thin white film. This film was removed by gentle scrubbing under water. The resulting dried BAC acrylate slides appeared clear and transparent with no visible residue.

Figure 5A:
FIGS. 5A–5C are photographs showing a N, N' bis(acryloyl)cystamine (BAC) acrylate slide after hybridization to fluorescent complementary oligonucleotide probes.

A BAC acrylate slide was then spotted with different concentrations ranging from 30 μM to 1 μM of beta-globin-specific 70 mer Acrydite™ modified oligonucleotide containing TCEP in the spotting solution. The spots were visualized by hybridization with Cy3 labeled globin cDNA (10 ng/80 ul) in 100 μl of 20×saline sodium phosphate EDTA buffer (SSPE; 3.6 M sodium chloride, 200 mM sodium phosphate, pH 7.4, 20 mM EDTA, pH 7.4) in a hybridization chamber. The visualized spots formed are shown in FIG. 5, a photograph of the BAC acrylate slide after hybridization to a fluorescent complementary oligonucleotide probe.

Figure 5B:
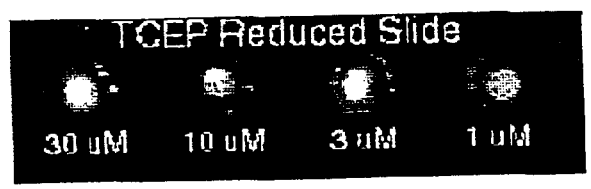
Figure 5C:
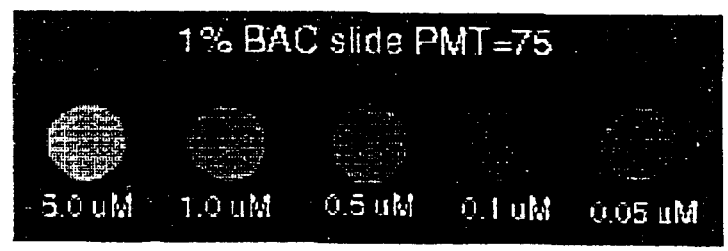

When the dried BAC acrylate slide were soaked in 50 mM TCEP for 30 minutes prior to spotting and TCEP was left out of the spotting solution, the results shown in FIG. 5B were obtained. When SDS at 0.01% in carbonate buffer (100 MM, pH 10.0) was used as the spotting buffer with the Acrydite™ modified oliogonucleotide on a dried BAC acrylate slide exposed to TCEP for 30 minutes prior to spotting, the results shown in FIG. 3C were obtained.

Example 15

Array Formation on a Mesh

A piece of nylon screen is placed between two silane treated glass plates. An edge of the nylon screen is allowed to extend from between the plates. A measured aliquot of the gel solution from Example 5 is placed on the extension and the solution is wicked onto the nylon screen between the two glass plates. The solution is allowed to gel. Prior to use the slide is activated and provided with Acrydite™ modified oligonucleotides as above.

Example 16

Use of Gel Matrix Coated Support

Provide a polyacrylamide gel matrix wherein the polyacrylamide matrix has thiol cross-linkages (no nucleic acid or protein probes) such as, for example, by following Example 5, Step 1. In addition to the reagents for forming the thiol-derivatized acrylamide gel solution, mix in a desired cell type for culture. For example, *E. coli* provided with nutrient culture reagents may be grown within the polymerized gel. To release the bacterial cells after replication has occurred, cleave the dithiols to the degree desired, for example by following the procedure described in Example 5, step 2 to release the cells.

Varying the amount of acrylamide cross linker used will allow regulation of the density of the gel.

Example 17

Use of Gel Matrix Probe Bearing Coated Glass Slide Support for Cloning and Amplification Following the procedure described in Example 5, Step 1 using a bisacrylamide cross-linker with bound Acrydite™ modified oligonucleotides having a desired primer sequence to provide a thiol derivatized acrylamide gel solution additionally having bound oligonucleotides. To this gel solution, add the reagents (to include a second primer in solution where desired; nucleic acids; enzyme) required to allow amplication by polymerase chain reaction cycling and a sample thought to contain the nucleic acid fragment to be amplified. Allow the gel solution to polymerize on a support such as the acrylate slide and expose the slide to PCR cycling conditions. Cleave the latent thiol groups using a procedure such as that described in Example 5, Step 2. Release and remove the amplified nucleic acid.

Example 18

Thin Layer Monomers Containing Disulfide Linkages For Immobilization of Nucleic Acids Acryl-silane coated microscope slides (Gel Associates, Inc., Houston, Tex.) were submerged in 0.1–2% heated BAC/water solution. 100–400 μl or 10% APS and 10% TEMED were added per 50 ml of solution for a rapid polymerization. Chain terminators, e.g., isopropanol, can be added prior to polymerization to induce short chain growth. N,N'methylenebisacrylamide (hereinafter "BIS") can be added to the BAC solution at the appropriate concentration prior to polymerization to allow multiple chain growth or polymer branching. Polymerization is complete within 5 minutes or upon the formation of a white particulate (polyBAC). The white particulate can be removed from the slides under water by a gentle hand scrub. Slides were suspended in 5–100 mM TCEP for reduction of disulfides. Thiol formation was immediately evident by development of a putrid odor. The slides were then dried for spotting.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of immobilizing an affinity ligand on a microarray comprising the steps of:

provinding a solid support comprising immobilized latent thiol groups by contacting an unsaturated aliphatic surface of the support with a polymerization solution and a polymerizable disulfide compound to form a polymer matrix;

activating the latent thiol groups by contacting the matrix with a disulfide reducing agent; and reacting the activated thiol groups with an affinity ligand having at least one α,β unsaturated carbonyl functional group to thereby immobilize the affinity ligand on a microarray.

2. The method of claim 1, wherein the ligand is selected from the group consisting of a nucleic acid, a modified nucleic acid and a nucleic acid analog.

3. The method of claim 2, wherein the latent thiol groups are activated and reacted with the affinity ligand upon contact of the solid support with the affinity ligand.

4. A method of preparing a solid support having immobilized thiol groups, comprising the steps of:

contacting a glass solid support with a silane compound represented by the following structural formula:

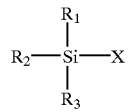

wherein:

X is a halogen; and $R_1$, $R_2$, and R3, are selected from the group consisting of a halogen, an alkyl group, an alkenyl group or a group having at least one α,β-unsaturated carbonyl, provided that at least one of $R_1$, $R_2$, or $R_3$ is an alkenyl group or a group having at least one α,β-unsaturated carbonyl, thereby forming a solid support having an unsaturated aliphatic surface;

thereafter contacting the unsaturated aliphatic surface of the solid support with a polymerization solution containing a free radical initiator and disulfide bisacrylamide represented by the following structural formula:

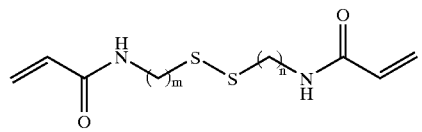

wherein:

n and m are each, independently, a positive integer, thereby forming a solid support comprising immobilized latent thiol groups; and thereafter contacting the latent thiol groups with a disulfide reducing agent, thereby forming a solid support having immobilized thiol groups.

5. The method of claim 4, wherein a plurality of nucleic acids are immobilized on the solid support.

6. The method of claim 5, wherein the solid support comprises two or more spatially distinct regions, each region comprising a plurality of immobilized nucleic acids.

7. The method of claim 6, wherein the latent thiol groups in selected regions of the support are activated, thereby providing a support comprising selected regions of reactive thiol groups.

8. The method of claim 4, wherein the thiol groups comprise disulfide groups.

9. The method of claim 4, wherein the polymerization solution further comprises an acrylamide.

* * * * *

UNITED STATES PATENT AND TRADEMARK OFFICE
CERTIFICATE OF CORRECTION

PATENT NO.   : 6,492,118 B1
DATED        : December 10, 2002
INVENTOR(S)  : Ezra S. Abrams et al.

It is certified that error appears in the above-identified patent and that said Letters Patent is hereby corrected as shown below:

Column 2,
Line 14, reads "can comprises two" and should read -- can comprise two --.
Lines 36-37, read "comprises" and should read -- comprise --.

Column 3,
Line 40, reads "($\alpha,\beta$-" and should read -- $\alpha\beta$ --. (*delete parenthesis*).
Line 64, reads "where in" and should read -- wherein --.

Column 4,
Line 11, reads "reducting" and should read -- reducing --.
Line 12, reads "shown if" and should read -- shown in --.

Column 6,
Line 10, reads "($\alpha,\beta$-" and should read -- $\alpha,\beta$- -- (*delete parenthesis*),
Line 20, reads "aliphatic surface of the solid support" and should read -- aliphatic surface of the solid support. -- (*missing period, end of sentence*).
Line 63, reads "m in are" and should read -- m are --.

Column 10,
Line 12, reads "($\alpha,\beta$-" and should read -- $\alpha,\beta$- -- (*delete parenthesis*).

Column 12,
Line 54, reads "Wetrnur" and should read -- Wetmur --.

Column 13,
Line 9, reads "temperate" and should read -- temperature --.
Line 27, reads "are antibody" and should read -- is antibody --.

Column 14,
Line 3, reads "nucleotides even" and should read -- nucleotides, even --.
Line 40, reads "$C_{18}$," and should read -- $C_{18}$ --.

Column 15,
Line 14, reads "has 5" and should read -- have 5 --.
Lines 28-29, reads "includes substituted or substituted alkyl" and should read -- includes substituted or unsubstituted alkyl --.
Line 51, reads "($\alpha,\beta$-" and should read -- $\alpha,\beta$- -- (*delete parenthesis*).

UNITED STATES PATENT AND TRADEMARK OFFICE
CERTIFICATE OF CORRECTION

PATENT NO. : 6,492,118 B1
DATED : December 10, 2002
INVENTOR(S) : Ezra S. Abrams et al.

It is certified that error appears in the above-identified patent and that said Letters Patent is hereby corrected as shown below:

Column 16,
Line 26, reads "with carboxylic" and should read -- with a carboxylic --.

Column 17,
Line 14, reads "rylamide" and should read -- acrylamide --.
Line 21, reads "which as" and should read -- which was --.
Line 23, reads "he Johns" and should read -- The Johns --.
Line 24, reads "et aL, and should read -- et al., --.
Line 27, reads "as hat" and should read -- as that --.
Line 52, reads "pol(yethylene" and should read -- poly(ethylene --.
Line 54, reads "The acronym "SATP is intended to encompass" and should read -- The acronym "SATP" is intended to compass -- (*second quotation mark missing*).

Column 18,
Line 6, reads "Hercules," and should read -- Hercules, Calif. --.
Line 51, reads "α,β-," and should read -- α,β -- (*delete parenthesis*).
Line 62, reads "on embodiment" and should read -- one embodiment --.

Column 19,
Lines 61 and 64, reads "Inc, Warrington PA" and should read -- Inc., Warrington, PA --.
Line 62, reads "pol(yethylene" and should read -- poly(ethylene --.

Column 20,
Line 2, reads "Inc, Warrington PA" and should read -- Inc., Warrington, PA --.
Line 6, reads "used improve" and should read -- used to improve --.
Line 39, reads "compound is represented" and should read -- compound represented --.
Line 66, reads "Superdex,." and should read -- Superdex. --

Column 21,
Lines 26-27, reads "substitued or aralkyl" and should read -- substitued or unsubstituted aralky --.

Column 21,
Line 43, reads "and Z, is" and should read -- and $Z_1$ is --.

Column 22,
Line 12, reads "set of components are" and should read -- set of components is --.
Line 34, reads "Discovery, Journal of" and should read -- Discovery," Journal of -- (*missing quotation mark*).
Line 37, reads "are intended" and should read -- is intended --.

UNITED STATES PATENT AND TRADEMARK OFFICE
CERTIFICATE OF CORRECTION

PATENT NO. : 6,492,118 B1
DATED : December 10, 2002
INVENTOR(S) : Ezra S. Abrams et al.

It is certified that error appears in the above-identified patent and that said Letters Patent is hereby corrected as shown below:

Column 24,
Line 28, reads "principle" and should read -- principal --.

Column 25,
Line 1, reads "HCI" and should read -- HCl --
Line 23, reads "HCL" and should read -- HCl --.
Line 40, reads "Exampel" and should read -- Example --.
Line 55, reads "25 FM" and should read -- 25$\mu$M --.

Column 26,
Lines 25-26, reads "covatently linked to an acrylamide-modified" and should read -- covatently linked to acrylamide-modified --.

Column 27,
Line 6, reads "I and II" and should read -- I and III --.
Line 26, reads "are important" and should read -- is important --.
Line 34, reads "BioRad laboratories" and should read -- BioRad Laboratories --.
Line 53, reads "can be also be" and should read -- can also be --.
Line 67, reads "mll" and should read -- III --.

Column 28,
Line 1, reads "NH2" and should read -- NH$_2$ --.
Line 11, reads "2% SDS was placed" and should read -- 2% SDS) was placed -- (*insert end of parenthesis*).
Liner 14, reads "Coming, Coming" and should read -- Corning, Corning --.
Line 22, reads "on an Gel-Coated" and should read -- on a Gel-Coated --.
Line 27, reads "solution)" and should read -- solution.) -- (*insert period before parenthesis*).
Lines 47-57, Table 1, Three (3) of the Table's Columns are misaligned. The "Probe" Column, should be blank. The "Replicate" Column should have the "Probe" Column's information/numbers underneath it. The "Pin #" Column should have the "Replicate" Column's information/numers underneath it.

Column 29,
Line 4, reads "90 III" and should read -- 90$\mu$1 --.
Line 5, reads "eDNA" and should read -- cDNA --.

Column 30,
Line 52, reads "placee" and should read -- placed --.

UNITED STATES PATENT AND TRADEMARK OFFICE
CERTIFICATE OF CORRECTION

PATENT NO. : 6,492,118 B1
DATED : December 10, 2002
INVENTOR(S) : Ezra S. Abrams et al.

It is certified that error appears in the above-identified patent and that said Letters Patent is hereby corrected as shown below:

Column 31,
Line 41, reads "bubbles or gaps in the solution." and should read -- bubbles or gaps in the solution. The solution was allowed -- (*"The solution was allowed" should not begin a new paragraph*).

Column 32,
Line 21, reads "humidity)" and should read -- humidity.) -- (*missing period before parenthesis*).
Line 32, reads "minutes. to" and should read -- minutes, to --.
Lines 37, reads "rabbit globin CDNA labeled" and should read -- rabbit globin cDNA labeled --.

Column 33,
Line 24, reads "MRNA" and should read -- mRNA --.

Column 34,
Line 1, reads "2%/BAC-" and should read -- 2% BAC --.
Line 21, reads "MRNA" and should read -- mRNA --.
Line 52, Table 3 header, reads "Background*" and should read -- Background** --.
Line 61, Table 3 footer, reads "*Background" and should read -- **Background --.

Column 35,
Line 19, reads "Slide 05" and should read -- Slide 03 --.
Line 25, reads "oligonucletide" and should read -- oligonucleotide --.
Line 63, reads "100MM" and should read -- 100mM --.

UNITED STATES PATENT AND TRADEMARK OFFICE
CERTIFICATE OF CORRECTION

PATENT NO.    : 6,492,118 B1
DATED         : December 10, 2002
INVENTOR(S)   : Ezra S. Abrams et al.

It is certified that error appears in the above-identified patent and that said Letters Patent is hereby corrected as shown below:

Column 36,
Line 18, reads "has thiol" and should read -- has dithiol --.

Column 38,
Line 1, reads "and R3" and should read -- and $R_3$ --.

Signed and Sealed this

Fourth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,492,118 B1
DATED : December 10, 2002
INVENTOR(S) : Ezra S. Abrams et al.

It is certified that error appears in the above-identified patent and that said Letters Patent is hereby corrected as shown below:

Column 2,
Line 14, reads "can comprises two" and should read -- can comprise two --.
Lines 36-37, read "comprises" and should read -- comprise --.

Column 3,
Line 40, reads "($\alpha,\beta$-" and should read -- $\alpha,,\beta$ --. (*delete parenthesis*).
Line 64, reads "where in" and should read -- wherein --.

Column 4,
Line 11, reads "reducting" and should read -- reducing --.
Line 12, reads "shown if" and should read -- shown in --.

Column 6,
Line 10, reads "($\alpha,\beta$-" and should read -- $\alpha,\beta$- -- (*delete parenthesis*),
Line 20, reads "aliphatic surface of the solid support" and should read -- aliphatic surface of the solid support. -- (*missing period, end of sentence*).
Line 63, reads "m in are" and should read -- m are --.

Column 10,
Line 12, reads "($\alpha,\beta$-" and should read -- $\alpha,\beta$- -- (*delete parenthesis*).

Column 12,
Line 54, reads "Wetrnur" and should read -- Wetmur --.

Column 13,
Line 9, reads "temperate" and should read -- temperature --.
Line 27, reads "are antibody" and should read -- is antibody --.

Column 14,
Line 3, reads "nucleotides even" and should read -- nucleotides, even --.
Line 40, reads "$C_{18}$," and should read -- $C_{18}$ --.

Column 15,
Line 14, reads "has 5" and should read -- have 5 --.
Lines 28-29, reads "includes substituted or substituted alkyl" and should read -- includes substituted or unsubstituted alkyl --.
Line 51, reads "($\alpha,\beta$-" and should read -- $\alpha,\beta$- -- (*delete parenthesis*).

UNITED STATES PATENT AND TRADEMARK OFFICE
CERTIFICATE OF CORRECTION

PATENT NO. : 6,492,118 B1
DATED : December 10, 2002
INVENTOR(S) : Ezra S. Abrams et al.

It is certified that error appears in the above-identified patent and that said Letters Patent is hereby corrected as shown below:

Column 16,
Line 26, reads "with carboxylic" and should read -- with a carboxylic --.

Column 17,
Line 14, reads "rylamide" and should read -- acrylamide --.
Line 21, reads "which as" and should read -- which was --.
Line 23, reads "he Johns" and should read -- The Johns --.
Line 24, reads "et aL, and should read -- et al., --.
Line 27, reads "as hat" and should read -- as that --.
Line 52, reads "pol(yethylene" and should read -- poly(ethylene --.
Line 54, reads "The acronym "SATP is intended to encompass" and should read -- The acronym "SATP" is intended to encompass -- (*second quotation mark missing*).

Column 18,
Line 6, reads "Hercules," and should read -- Hercules, Calif. --.
Line 51, reads "α,β-," and should read -- α,β- -- (*delete parenthesis*).
Line 62, reads "on embodiment" and should read -- one embodiment --.

Column 19,
Lines 61 and 64, reads "Inc, Warrington PA" and should read -- Inc., Warrington, PA --.
Line 62, reads "pol(yethylene" and should read -- poly(ethylene --.

Column 20,
Line 2, reads "Inc, Warrington PA" and should read -- Inc., Warrington, PA --.
Line 6, reads "used improve" and should read -- used to improve --.
Line 39, reads "compound is represented" and should read -- compound represented --.
Line 66, reads "Superdex,." and should read -- Superdex. --

Column 21,
Lines 26-27, reads "substitued or aralkyl" and should read -- substituted or unsubstituted aralkyl --.

Column 21,
Line 43, reads "and Z, is" and should read -- and $Z_1$ is --.

Column 22,
Line 12, reads "set of components are" and should read -- set of components is --.
Line 34, reads "Discovery, Journal of" and should read -- Discovery," Journal of -- (*missing quotation mark*).
Line 37, reads "are intended" and should read -- is intended --.

UNITED STATES PATENT AND TRADEMARK OFFICE
CERTIFICATE OF CORRECTION

PATENT NO.    : 6,492,118 B1
DATED         : December 10, 2002
INVENTOR(S)   : Ezra S. Abrams et al.

It is certified that error appears in the above-identified patent and that said Letters Patent is hereby corrected as shown below:

Column 24,
Line 28, reads "principle" and should read -- principal --.

Column 25,
Line 1, reads "HCI" and should read -- HCl --
Line 23, reads "HCL" and should read -- HCI --.
Line 40, reads "Exampel" and should read -- Example --.
Line 55, reads "25 FM" and should read -- 25$\mu$M --.

Column 26,
Lines 25-26, reads "covatently linked to an acrylamide-modified" and should read -- covatently linked to acrylamide-modified --.

Column 27,
Line 6, reads "I and II" and should read -- I and III --.
Line 26, reads "are important" and should read -- is important --.
Line 34, reads "BioRad laboratories" and should read -- BioRad Laboratories --.
Line 53, reads "can be also be" and should read -- can also be --.
Line 67, reads "mll" and should read -- III --.

Column 28,
Line 1, reads "NH2" and should read -- $NH_2$ --.
Line 11, reads "2% SDS was placed" and should read -- 2% SDS) was placed -- (*insert end of parenthesis*).
Line 14, reads "Coming, Coming" and should read -- Corning, Corning --.
Line 22, reads "on an Gel-Coated" and should read -- on a Gel-Coated --.
Line 27, reads "solution)" and should read -- solution.) -- (*insert period before parenthesis*).
Lines 47-57, Table 1, Three (3) of the Table's Columns are misaligned. The "Probe" Column, should be blank. The "Replicate" Column should have the "Probe" Column's information/numbers underneath it. The "Pin #" Column should have the "Replicate" Column's information/numers underneath it.

Column 29,
Line 4, reads "90 III" and should read -- 90$\mu$1 --.
Line 5, reads "eDNA" and should read -- cDNA --.

Column 30,
Line 52, reads "placee" and should read -- placed --.

UNITED STATES PATENT AND TRADEMARK OFFICE
CERTIFICATE OF CORRECTION

PATENT NO.    : 6,492,118 B1
DATED         : December 10, 2002
INVENTOR(S)   : Ezra S. Abrams et al.

It is certified that error appears in the above-identified patent and that said Letters Patent is hereby corrected as shown below:

Column 31,
Line 41, reads "bubbles or gaps in the solution." and should read -- bubbles or gaps in the solution. The solution was allowed -- (*"The solution was allowed" should not begin a new paragraph*).

Column 32,
Line 21, reads "humidity)" and should read -- humidity.) -- (*missing period before parenthesis*).
Line 32, reads "minutes. to" and should read -- minutes, to --.
Lines 37, reads "rabbit globin CDNA labeled" and should read -- rabbit globin cDNA labeled --.

Column 33,
Line 24, reads "MRNA" and should read -- mRNA --.

Column 34,
Line 1, reads "2%/BAC-" and should read -- 2% BAC --.
Line 21, reads "MRNA" and should read -- mRNA --.
Line 52, Table 3 header, reads "Background*" and should read -- Background** --.
Line 61, Table 3 footer, reads "*Background" and should read -- **Background --.

Column 35,
Line 19, reads "Slide 05" and should read -- Slide 03 --.
Line 25, reads "oligonucletide" and should read -- oligonucleotide --.
Line 63, reads "100MM" and should read -- 100mM --.

UNITED STATES PATENT AND TRADEMARK OFFICE
CERTIFICATE OF CORRECTION

PATENT NO.    : 6,492,118 B1
DATED         : December 10, 2002
INVENTOR(S)   : Ezra S. Abrams et al.

It is certified that error appears in the above-identified patent and that said Letters Patent is hereby corrected as shown below:

<u>Column 36,</u>
Line 18, reads "has thiol" and should read -- has dithiol --.

<u>Column 38,</u>
Line 1, reads "and R3" and should read -- and $R_3$ --.

This certificate supersedes Certificate of Correction issued January 4, 2005.

Signed and Sealed this

Tenth Day of May, 2005

JON W. DUDAS
*Director of the United States Patent and Trademark Office*